United States Patent [19]

Swain et al.

[11] Patent Number: 5,629,347

[45] Date of Patent: May 13, 1997

[54] AROMATIC COMPOUNDS, PHARMACEUTICAL COMPOSITIONS CONTAINING THEM AND THEIR USE IN THERAPY

[75] Inventors: Christopher J. Swain, Cambridge; Martin R. Teall, Stansted; Brian J. Williams, Great Dunmow, all of United Kingdom

[73] Assignee: Merck Sharp & Dohme Ltd., Hoddesdon, England

[21] Appl. No.: 170,190

[22] PCT Filed: Jul. 3, 1992

[86] PCT No.: PCT/GB92/01213

§ 371 Date: Oct. 20, 1994

§ 102(e) Date: Oct. 20, 1994

[87] PCT Pub. No.: WO93/01160

PCT Pub. Date: Jan. 21, 1993

[30] Foreign Application Priority Data

Jul. 5, 1991 [GB] United Kingdom ............ 9114554
Jul. 10, 1991 [GB] United Kingdom ............ 9114886
Mar. 11, 1992 [GB] United Kingdom ............ 9205294

[51] Int. Cl.[6] ............... A61K 31/165; C07C 233/05
[52] U.S. Cl. ............ 514/620; 514/521; 514/522; 514/534; 514/535; 514/539; 514/586; 514/619; 514/618; 514/617; 514/616; 514/886; 514/478; 558/414; 560/9; 560/11; 560/12; 560/13; 560/24; 560/36; 564/152; 564/153; 564/154; 564/155

[58] Field of Search ............ 564/164, 165, 564/402, 404, 152, 153, 154, 155, 156, 405, 376; 514/619, 620, 617, 616, 618, 886, 622, 534, 535, 539, 521, 522, 586, 478; 558/414; 560/9, 11, 12, 13, 24, 36

[56] References Cited

FOREIGN PATENT DOCUMENTS

0394989A3 10/1990 European Pat. Off.
0415413A1 3/1991 European Pat. Off.
2035535 7/1969 Germany.
2054588 2/1981 United Kingdom.

OTHER PUBLICATIONS

J. of Org. Chem., vol. 23, No. 11 pp. 1815–1816 (Nov. 1958), by R. Filler, et al.
J. of Org. Chem., vol. 27, No. 7, pp. 2406–2411 (Jul. 1962), by A. Mustafa, et al.
J. Med. Chem., vol. 32, No. 4 (1989), by K. Hsieh, et al.

*Primary Examiner*—Shailendra Kumar
*Attorney, Agent, or Firm*—Robert J. North; Melvin Winokur

[57] ABSTRACT

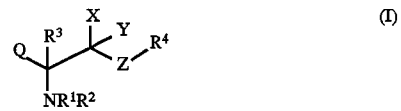

Compounds of formula (I), and salts and prodrugs thereof, wherein Q is $R^9CR^{10}R^{11}$ or $CH_2R^9CR^{10}R^{11}$ where $R^9$ is H or OH and $R^{10}$ and $R^{11}$ are optionally substituted phenyl, optionally substituted benzyl, $C_{5-7}$cycoalkyl or ($C_{5-7}$cycloalkyl)methyl; $R^1$ and $R^2$ are H, optionally substituted $C_{1-6}$alkyl, optionally substituted phenyl($C_{1-4}$alkyl), $C_{2-6}$alkenyl, $C_{2-6}$alkynyl, $COR^a$, $COOR^a$, $COC_{1-6}$alkylhalo, $COC_{1-6}$alkylNR$^a$R$^b$, $CONR^{12}C_{1-6}$alkylCONR$^a$R$^b$, $CONR^aR^b$, or $SO_2R^a$, or $R^1$ and $R^2$ together form a chain $(CH_2)_q$ optionally substituted by oxo where one methylene group may optionally be replaced by O or NR$^x$; $R^3$ is H, $C_{1-6}$alkyl or $C_{2-6}$alkenyl; $R^4$ is optionally substituted phenyl($C_{1-3}$alkyl); X and Y are H, or X and Y together are =O; and Z is O, S, or NR$^7$; are tachykinin antagonists. They and compositions thereof are useful in therapy.

12 Claims, No Drawings

AROMATIC COMPOUNDS, PHARMACEUTICAL COMPOSITIONS CONTAINING THEM AND THEIR USE IN THERAPY

This application is a 371 of PCT/GB92/01213 filed Jan. 21, 1993.

This invention relates to a class of aromatic compounds which are useful as tachykinin antagonists. More particularly, the compounds of the invention contain a diphenyl or like moiety and a substituted or unsubstituted amine moiety.

The tachykinins are a group of naturally occurring peptides found widely distributed throughout mammalian tissues, both within the central nervous system and in peripheral nervous and circulatory systems.

The structures of three known mammalian tachykinins are as follows:

Substance P:

Arg-Pro-Lys-Pro-Gln-Gln-Phe-Phe-Gly-Leu-Met-$NH_2$

Neurokinin A:

His-Lys-Thr-Asp-Ser-Phe-Val-Gly-Leu-Met-$NH_2$

Neurokinin B:

Asp-Met-His-Asp-Phe-Phe-Val-Gly-Leu-Met-$NH_2$

For example, substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS (Dec. 1987) 8 506–510], specifically in the transmission of pain in migraine (B. E. B. Sandberg et al, J. Med Chem, (1982) 25 1009) and in arthritis [Levine et al in Science (1984) 226 547–549]. These peptides have also been implicated in gastrointestinal (GI) disorders and diseases of the GI tract such as inflammatory bowel disease [Mantyh et al in Neuroscience (1988) 25 (3) 817–37 and D. Regoli in "Trends in Cluster Headache"Ed. Sicuteri et al Elsevier Scientific Publishers, Amsterdam (1987) page 85)]. It is also hypothesised that there is a neurogenic mechanism for arthritis in which substance P may play a role [Kidd et al "A Neurogenic Mechanism for Symmetrical Arthritis" in The Lancet, 11 Nov. 1989 and Grönblad et al "Neuropeptides in Synovium of Patients with Rheumatoid Arthritis and Osteoarthritis" in J. Rheumatol. (1988) 15(12) 1807–10]. Therefore, substance P is believed to be involved in the inflammatory response in diseases such as rheumatoid arthritis and steoarthritis, and fibrositis [O'Byrne et al in Arthritis and Rheumatism (1990) 33 1023–8]. Other disease areas where tachykinin antagonists are believed to be useful are allergic conditions [Hamelet et al Can. J. Pharmacol. Physiol. (1988) 66 1361–7], immunoregulation [Lotz et al Science (1988) 241 1218–21 and Kimball et al, J. Immunol. (1988) 241 (10) 3564–9] vasodilation, bronchospasm, reflex or neuronal control of the viscera [Mantyh et al, PNAS (1988) 85 3235–9] and, possibly by arresting or slowing β-amyloid-mediated neurodegenerative changes [Yankner et al Science (1990) 250, 279–82] in senile dementia of the Alzheimer type, Alzheimer's disease and Downs Syndrome. Substance P may also play a role in demyelinating diseases such as multiple sclerosis and amyotrophic lateral sclerosis [J. Luber-Narod et. al., poster to be presented at C.I.N.P. XVIIIth Congress, 28th Jun.–2nd Jul., 1992, in press], and in disorders of bladder function such as bladder detrusor hyper-reflexia (Lancet, 16th May, 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent application no. 0 436 334), opthalmic disease such as conjuctivitis, vernal conjunctivitis, and the like, and cutaneous diseases such as contact dermatitis, atropic dermatitis, urticaria, and other eczematoid dermatitis (European patent application no. 0 394 989).

We have now found a class of non-peptides which are potent antagonists of tachykinin.

The following compounds are known: DL-diphenylalanine benzyl ester hydrochloride salt (J. Med. Chem, 32(4), 898 (1989)); 2-benzamido-3,3-diphenylpropanoyl benzamide (J. Org. Chem., 23, 1815 (1958)); 2-benzamido-3,4-diphenyl-butanoyl benzamide (J. Org. Chem., 27, 2406 (1962)).

Patent protection is therefore not sought for these compounds per se. Pharmaceutical compositions containing the compounds, or the compounds for use in therapy have not previously been disclosed and are within the ambit of the present invention.

European patent application no. 330 940 discloses compounds of formula (1):

$$R^1-Z-Y-O-CH_2-CH-CH_2 \overset{X}{\underset{R^6}{\underset{|}{-}}} R^5 \quad (1)$$
$$\underset{R^2 \diagdown N \diagup R^3}{|}$$

wherein:

$R^1$ is inter alia an aromatic group;

$R^2$ and $R^3$ are $C_{1-6}$aliphatic, or together form a ring which may contain further heteroatoms;

$R^4$ is an aromatic group;

$R^5$ is inter alia an aromatic group;

$R^6$ is inter alia H;

X is a bond or $CH_2$;

Y is inter alia $C_{1-6}$hydrocarbyl;

Z is inter alia a bond.

The compounds are said to have anti-depressant effect in mice.

British patent no. 1377350 discloses compounds of formula (2):

(2)

wherein:

R is $C_{1-4}$alkyl;

$R^1$ is inter alia H or lower alkyl;

3

$R^2$ is inter alia an aralkenyl group; and $R^3$ is H or $CH_3$.

The compounds are said to be morphine antagonists and to have analgesic activity.

The present invention provides a compound of formula (I), or a salt or prodrug thereof:

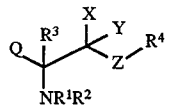

wherein

Q represents $R^9CR^{10}R^{11}$ where $R^9$ is H or hydroxy and $R^{10}$ and $R^{11}$ each independently represent optionally substituted phenyl, optionally substituted benzyl, $C_{1-7}$cycloalkyl or ($C_{5-7}$cycloalkyl)methyl;

$R^1$ and $R^2$ independently represent H; $C_{1-6}$ alkyl optionally substituted by hydroxy, cyano, $COR^a$, $COOR^a$, $CONR^aR^b$, $COC_{1-6}$alkyl$NR^aR^b$, $CONR^{12}C_{1-6}$alkyl$OR^a$, $CONR^{12}C_{1-6}$alkyl$CONR^aR^b$ or $NR^aR^b$ (where $R^a$ and $R^b$ each independently represent H, $C_{1-6}$ alkyl, phenyl (optionally substituted by one or more of $C_{1-6}$alkyl, $C_{1-6}$alkoxy, halo and trifluoromethyl), phenyl($C_{1-4}$alkyl) (optionally substituted in the phenyl ring by one or more of $C_{1-6}$ alkyl, $C_{1-6}$ alkoxy, halo and trifluoromethyl) or $R^a$ and $R^b$ together form a chain $(CH_2)_p$ optionally substituted by oxo where p is 4 or 5 and where one methylene group may optionally be replaced by an oxygen atom or a group $NR^x$, where $R^x$ is H or $C_{1-6}$ alkyl, and $R^{12}$ represents H, $C_{1-6}$alkyl, phenyl (optionally substituted by one or more of $C_{1-6}$alkyl, $C_{1-6}$alkoxy, halo and trifluoromethyl) or phenyl($C_{1-4}$alkyl) (optionally substituted in the phenyl ring by one or more of $C_{1-6}$alkyl, $C_{1-6}$alkoxy, halo and trifluoromethyl); phenyl($C_{1-4}$ alkyl) (optionally substituted by one or more of $C_{1-6}$ alkyl, $C_{1-6}$ alkoxy, halo and trifluoromethyl in the phenyl ring); $C_{2-6}$ alkenyl; $C_{2-6}$ alkynyl; $COR^a$; $COOR^a$; $COC_{1-6}$alkylhalo; $COC_{1-6}$alkyl$NR^aR^b$; $CONR^{12}C_{1-6}$alkyl$CONR^aR^b$; $CONR^aR^b$; or $SO_2R^a$; (where $R^a$, $R^b$ and $R^{12}$ are as previously defined) or $R^1$ and $R^2$ together form a chain $(CH_2)_q$ optionally substituted by oxo where q is 4 or 5 and where one methylene group may optionally be replaced by an oxygen atom or a group $NR^x$, where $R^x$ is H or $C_{1-6}$ alkyl;

$R^3$ represents H, $C_{1-6}$ alkyl or $C_{2-6}$alkenyl;

$R^4$ represents $C_{1-3}$ alkyl substituted by a phenyl group which may itself optionally be substituted by one or more of $C_{1-6}$ alkyl, $C_{2-6}$ alkenyl, $C_{2-6}$ alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ and $CONR^cR^d$, where $R^c$ and $R^d$ independently represent H, $C_{1-6}$ alkyl, phenyl or trifluoromethyl;

X and Y each represent H, or X and Y together represent a group =O; and

Z represents O, S, or $NR^7$, where $R^7$ represents H or $C_{1-6}$ alkyl;

with the exception of DL-diphenylalanine benzyl ester hydrochloride salt; 2-benzamido-3,3-diphenylpropanoyl benzamide; and 2-benzamido-3,4-diphenyl-butanoyl benzamide.

The alkyl, alkenyl and alkynyl groups referred to with respect to any of the formulae herein may represent straight, branched or cyclic groups. Thus, for example, suitable alkyl

4 groups include methyl, ethyl, n- or isopropyl, n-, sec-, iso- or tert-butyl, cyclopropyl, cyclobutyl, cyclopentyl or cyclohexyl, and cycloalkylalkyl groups such as cyclopropylmethyl; suitable alkenyl groups include vinyl and allyl; and suitable alkynyl groups include propargyl.

For alkylphenyl substituents, the alkyl moiety may be straight or branched.

The term "halo" as used herein includes fluoro, chloro, bromo and iodo.

Where $R^{10}$ and/or $R^{11}$ represent substituted phenyl or benzyl groups, suitable substituents include 1, 2 or 3 substituents selected from $C_{1-6}$alkyl, $C_{1-6}$alkoxy, halo and trifluoromethyl.

In one embodiment, the present invention provides compounds of formula (Ia)

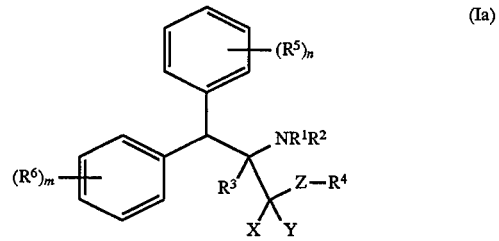

wherein $R^1$ and $R^2$ independently represent H; $C_{1-6}$ alkyl optionally substituted by hydroxy, cyano, $COR^{13}$, $COOR^{13}$, $CONR^{13}R^{14}$, $COC_{1-4}$alkyl$NR^{13}R^{14}$, $CONR^{13}C_{1-4}$alkyl$OR^{14}$, $CONR^{13}C_{1-4}$alkyl$CONR^{13}R^{14}$ or $NR^{13}R^{14}$ (where $R^{13}$ and $R^{14}$ each independently represent H, $C_{1-6}$ alkyl, phenyl (optionally substituted by one or more of $C_{1-6}$alkyl, $C_{1-6}$alkoxy, halo and trifluoromethyl), or phenyl($C_{1-4}$alkyl) (optionally substituted in the phenyl ring by one or more of $C_{1-6}$ alkyl, $C_{1-6}$ alkoxy, halo and trifluoromethyl); phenyl($C_{1-4}$ alkyl) (optionally substituted by one or more of $C_{1-6}$ alkyl, $C_{1-6}$ alkoxy, halo and trifluoromethyl in the phenyl ring); $C_{2-6}$ alkenyl; $C_{2-6}$ alkynyl; $COR^{13}$; $COOR^{13}$; $CONHR^{13}$; $COC_{1-4}$alkyl$NR^{13}R^{14}$; $CONR^{13}C_{1-4}$alkyl$CONR^{13}R^{14}$; $CONR^{13}R^{14}$; or $SO_2R^{13}$; (where $R^{13}$ and $R^{14}$ are as previously defined) or $R^1$ and $R^2$ together form a chain $(CH_2)_q$ where q is 4 or 5 and where one non-terminal methylene group may optionally be replaced by an oxygen atom or a group $NR^x$, where $R^x$ is H or $C_{1-6}$ alkyl;

$R^3$ represents H or $C_{1-6}$ alkyl;

$R^4$ represents $C_{1-3}$ alkyl substituted by a phenyl group which may itself optionally be substituted by one or more of $C_{1-6}$ alkyl, $C_{2-6}$ alkenyl, $C_{2-6}$ alkynyl, halo, cyano, nitro, trifluoromethyl, trimethylsilyl, $SCH_3$, $SOCH_3$, $SO_2CH_3$, $OR^c$, $NR^cR^d$, $NR^cCOR^d$, $NR^cCOOR^d$, $COOR^c$ and $CONR^cR^d$, where $R^c$ and $R^d$ independently represent H, $C_{1-6}$ alkyl, phenyl or trifluoromethyl.

each $R^5$ independently represents $C_{1-6}$ alkyl, $C_{1-6}$ alkoxy, halo or trifluoromethyl;

each $R^6$ independently represents $C_{1-6}$ alkyl, $C_{1-6}$ alkoxy, halo or trifluoromethyl;

n and m each represent 0, 1, 2 or 3;

X and Y each represent H, or X and Y together represent a group =O; and

Z represents O, S, or $NR^7$, where $R^7$ represents H or $C_{1-6}$ alkyl;

and salts and prodrugs thereof, with the exception of:

DL-diphenylalanine benzyl ester; and 2-benzamido-3,3-diphenylpropanoyl benzamide.

A particular sub group of compounds within this embodiment are compounds wherein $R^1$ and $R^2$ independently represent H, $C_{1-6}$ alkyl, phenyl($C_{1-4}$ alkyl), (optionally substituted by one or more of $C_{1-6}$ alkyl, $C_{1-6}$ alkoxy, halo and trifluoromethyl in the phenyl ring), $COR^{15}$, $COOR^{15}$ or $CONHR^{15}$, where $R^{15}$ is $C_{1-6}$ alkyl or phenyl (optionally substituted by one or more of $C_{1-6}$ alkyl, $C_{1-6}$ alkoxy, halo and trifluoromethyl); and $R^4$ represents $C_{1-3}$ alkyl substituted by a phenyl group which may itself optionally be substituted by one or more of $C_{1-6}$ alkyl, $C_{2-6}$ alkenyl, $C_{2-6}$ alkynyl, halo, cyano, nitro, trifluoromethyl, $SCH_3$, $SOCH_3$, $SO_2CH_3$, $OR^c$, $NR^cR^d$, $NR^cCOR^d$, $NR^cCOOR^d$, $COOR^c$ and $CONR^cR^d$, where $R^c$ and $R^d$ independently represent H, $C_{1-6}$ alkyl, phenyl or trifluoromethyl.

It is preferred that $R^9$ represents H. It is further preferred that at least one of $R^{10}$ and $R^{11}$ represents optionally substituted phenyl. More preferably, one of $R^{10}$ and $R^{11}$ represents optionally substituted phenyl and the other is selected from optionally substituted phenyl and optionally substituted benzyl. Where $R^{10}$ and $R^{11}$ represent optionally substituted phenyl or optionally substituted benzyl they will preferably represent unsubstituted phenyl or unsubstituted benzyl. It is particularly preferred that $R^{10}$ and $R^{11}$ both represent optionally substituted phenyl, especially unsubstituted phenyl.

Suitable values for the groups $R^1$ and $R^2$ include H; $C_{1-6}$ alkyl (especially methyl, ethyl, propyl, and cyclopropylmethyl); $C_{1-6}$alkyl substituted by, for example, cyano, hydroxy, $NH_2$, $CO_2C_{1-6}$alkyl, $CO_2H$, $CONR^aR^b$, $CONR^{12}C_{1-6}$alkyl$OR^a$, especially $CONHC_{1-6}$alkylOH, $CONR^{12}C_{1-6}$alkyl$NR^aR^b$, especially $CONHCH_2CH_2N(CH_3)_2$, and $CONR_{12}C_{1-6}$alkyl$CONR^aR^b$, especially $CONHCH_2CONH_2$; $SO_2R^a$, especially $SO_2CH_3$; $COR^a$, especially $CO(C_{1-6}$alkyl) and $CO(C_6H_5)$; $CO_2C_{1-4}$alkyl; $CONR^aR^b$; $COC_{1-4}$alkylhalo, especially $COCH_2Cl$; $COC_{1-6}$alkyl$NR^aR^b$, especially $COCH_2NR^aR^b$ such as $COCH_2NH_2$ or $COCH_2N(CH_3)_2$; $C_{1-6}$ alkenyl, especially allyl; and chains such as $(CH_2)_4$, $(CH_2)_5$, $(CH_2)_2O(CH_2)_2$ and $(CH_2)_2NHCOCH_2$.

In one preferred group of compounds according to the invention $R^1$ and $R^2$ are each independently H or $C_{1-6}$alkyl, especially H or methyl. Particularly preferred within this group are compounds wherein $R^1$ and $R^2$ both represent methyl.

In a further preferred group of compounds according to the invention, at least one of $R^1$ and $R^2$ represents an alkyl chain selected from $CH_2$, $CH(CH_3)$, $C(CH_3)_2$, $CH(CH_2CH_3)$, $C(CH_3)(CH_2CH_3)$, $CH(CH_2CH_2CH_3)$ and $CH(CH(CH_3)_2)$, preferably $CH_2$ or $CH(CH_3)$, substituted by a group selected from cyano, $CO_2H$, $CO_2C_{1-6}$alkyl, $CONR^aR^b$, $CONR^{12}C_{1-4}$alkyl$CONR^aR^b$ and $CONR^{12}C_{1-4}$alkyl$OR^a$, or $R^1$ and $R^2$ together form a chain $(CH_2)_q$, as defined for formula (I) above, wherein preferably one of the non-terminal methylene groups is replaced by a group $NR^x$, such as NH, and one of the carbon atoms of the chain is substituted by oxo.

The compounds of this preferred group have the advantage that they exhibit particularly low levels of activity at calcium channel receptors.

Within this preferred groups of compounds, where at least one of $R^1$ and $R^2$ represents $C_{1-4}$ straight or branched chain alkyl substituted by a group $CONR^aR^b$, preferably at least one of $R^a$ and $R^b$ is other than H and is more preferably $C_{1-6}$alkyl, such as methyl, and the other of $R^1$ and $R^2$ is preferably other than H and is more preferably $C_{1-6}$alkyl, such as methyl.

A further sub-group of compounds which possess the advantage of low calcium channel activity mentioned above is represented by compounds wherein at least one of $R^1$ and $R^2$ represents an alkyl chain selected from $CH_2$, $CH(CH_3)$, $C(CH_3)_2$, $CH(CH_2CH_3)$, $C(CH_3)(CH_2CH_3)$, $CH(CH_2CH_2CH_3)$ and $CH(CH(CH_3)_2)$, preferably $CH_2$ or $CH(CH_3)$, substituted by a group $CONR^{12}C_{1-4}$alkyl$NR^aR^b$, such as, for example, $CONHC_{1-4}$alkyl$NH(C_{1-4}$alkyl), or $CONHC_{1-4}$alkyl$N(C_{1-4}$alkyl)$_2$.

Suitable values for the group $R^3$ include H and methyl, preferably H.

Suitably $R^4$ represents a $C_{1-3}$ alkyl chain bearing a substituent which is a substituted phenyl group. Suitable phenyl substituents include methyl, methoxy, nitro, cyano, halo and trifluoromethyl. Preferably $R^4$ represents methyl substituted by a substituted phenyl group. Preferably one or two substituents will be present in the phenyl ring. More preferably $R^4$ represents methyl substituted by 3,5-disubstitutedphenyl. Particularly preferred are compounds wherein $R^4$ represents methyl substituted by 3,5-dimethylphenyl or 3,5-bistrifluoromethylphenyl.

Preferably X and Y each represent H.

Suitably Z represents oxa or a group NH. Preferably Z represents oxa.

A preferred sub-class of compounds according to the invention is represented by formula (Ib):

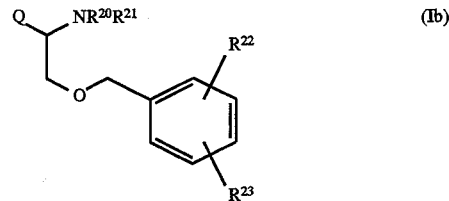

wherein

Q is as defined for formula (I) above, preferably benzhydryl (CH(phenyl)$_2$);

$R^{20}$ and $R^{21}$ each independently represent H; $C_{1-6}$ alkyl optionally substituted by hydroxy, cyano, $COR^a$, $COOR^a$, $CONR^aR^b$, $COC_{1-6}$alkyl$NR^aR^b$, $CONR^{12}C_{1-6}$alkyl$OR^a$, $CONR^{12}C_{1-6}$alkyl$CONR^aR^b$ or $NR^aR^b$, where $R^a$ and $R^b$ each independently represent H, $C_{1-6}$ alkyl, phenyl (optionally substituted by one or more of $C_{1-6}$alkyl, $C_{1-6}$alkoxy, halo and trifluoromethyl), phenyl($C_{1-4}$alkyl) (optionally substituted in the phenyl ring by one or more of $C_{1-6}$ alkyl, $C_{1-6}$ alkoxy, halo and trifluoromethyl) or $R^a$ and $R^b$ together form a chain $(CH_2)_p$ optionally substituted by oxo where p is 4 or 5 and where one methylene group may optionally be replaced by an oxygen atom or a group $NR^x$ where $R^x$ is as above defined, and $R^{12}$ is H, $C_{1-6}$alkyl, phenyl (optionally substituted by one or more of $C_{1-6}$alkyl, $C_{1-6}$alkoxy, halo and trifluoromethyl); or phenyl($C_{1-4}$alkyl) (optionally substituted in the phenyl ring by one or more of $C_{1-6}$alkyl, $C_{1-6}$alkoxy, halo and trifluoromethyl); phenyl($C_{1-4}$alkyl) (optionally substituted by one or more of $C_{1-6}$alkyl, $C_{1-6}$alkoxy, halo or trifluoromethyl in the phenyl ring); $C_{2-6}$ alkenyl; $C_{2-6}$alkynyl; $COR^a$; $COOR^a$; $COC_{1-6}$alkylhalo; $COC_{1-6}$alkyl$NR^aR^b$; $CONR^{12}C_{1-6}$alkyl$CONR^aR^b$; $CONR^aR^b$ or $SO_2R^a$, where $R^a$ and $R^b$ are as previously defined, or $R^{20}$ and $R^{21}$ together form a chain $(CH_2)_q$ where q is 4 or 5 and where one methylene group may optionally be replaced by an oxygen atom or a group $NR^x$ where $R^x$ is as above defined;

$R^{22}$ and $R^{23}$ each independently represent H, $C_{1-6}$ alkyl, $C_{2-6}$ alkenyl, halo, cyano, nitro, trifluoromethyl, trimethylsilyl, $SR^c$, $SOR^c$, $SO_2R^c$, $OR^c$, $NR^c$, $R^d$, $NR^cCOR^d$, $NR^cCOOR^d$, $COOR^c$ or $CONR^cR^d$, where $R^c$ and $R^d$ are as previously defined;
and salts and prodrugs thereof.

One sub-group of compounds of formula (Ib) is represented by compounds of formula (Ic),

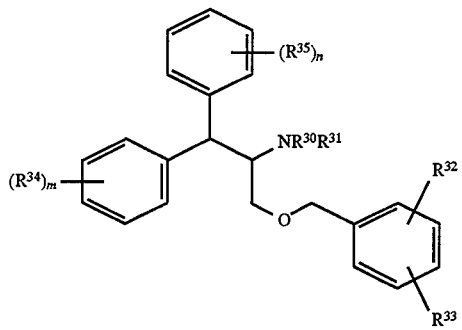

wherein
$R^{30}$ and $R^{31}$ each independently represent H; $C_{1-4}$alkyl optionally substituted by hydroxy, cyano, $COR^{13}$, $COOR^{13}$, $CONR^{13}R^{14}$, $COC_{1-4}$alkyl$NR^{13}R^{14}$, $CONR^{13}C_{1-4}$alkyl$OR^{14}$, $CONR^{13}C_{1-4}$alkyl$CONR^{13}R^{14}$ or $NR^{13}R^{14}$ (where $R^{13}$ and $R^{14}$ are as defined for formula (Ia) above); $C_{2-4}$ alkenyl; $C_{2-6}$ alkynyl; $COR^{13}$, $COOR^{13}$, $CONHR^{13}$, $COC_{1-4}$alkyl$NR^{13}R^{14}$, $CONR^{13}C_{1-4}$alkyl$CONR^{13}R^{14}$, $CONR^{13}R^{14}$ or $SO_2R^{13}$ (where $R^{13}$ and $R^{14}$ are as previously defined), or $R^{30}$ and $R^{31}$ together form a chain $(CH_2)_q$ as previously defined;

$R^{32}$ and $R^{33}$ each independently represent H, $C_{1-6}$ alkyl, $C_{2-6}$ alkenyl, $C_{1-6}$ alkoxy, halo, cyano, nitro, trifluoromethyl, trimethylsilyl, hydroxy, phenoxy or amino; and n and m are as previously defined;
and salts and prodrugs thereof.

A sub class of compounds of formula (Ic) is represented by compounds wherein $R^{30}$ and $R^{31}$ independently represent H, $C_{1-6}$ alkyl, phenyl($C_{1-4}$ alkyl), (optionally substituted by one or more of $C_{1-6}$ alkyl, $C_{1-6}$ alkoxy, halo and trifluoromethyl in the phenyl ring), $COR^{36}$, $COOR^{36}$ or $CONHR^{36}$, where $R^{36}$ is $C_{1-6}$ alkyl or phenyl (optionally substituted by one or more of $C_{1-6}$ alkyl, $C_{1-6}$ alkoxy, halo and trifluoromethyl).

One preferred group of compounds of formula (Ib) are compounds wherein at least one of $R^{20}$ and $R^{21}$ represents an alkyl chain selected from $CH_2$, $CH(CH_3)$, $C(CH_3)_2$, $CH(CH_2CH_3)$, $C(CH_3)(CH_2CH_3)$, $CH(CH_2CH_2CH_3)$ and $CH(CH(CH_3)_2)$, preferably $CH_2$ or $CH(CH_3)$, substituted by group selected from cyano, $CO_2H$, $CO_2(C_{1-6}$alkyl), $SO_2R^a$, $CONR^aR^b$, $CONR^{12}C_{1-4}$alkyl$CONR^aR^b$ or $CONHC_{1-4}$alkyl$OR^a$, or $R^{20}$ and $R^{21}$ together form a chain $(CH_2)_q$, as defined for formula (I) above, wherein preferably one of the non-terminal methylene groups is replaced by a group $NR^x$, such as NH, and one of the carbon atoms of the chain is substituted by oxo.

A further preferred group of compounds of formula (Ib) are compounds wherein at least one of $R^{20}$ and $R^{21}$ represents an alkyl chain selected from $CH_2$, $CH(CH_3)$, $C(CH_{32})$, $CH(CH_2CH_3)$, $C(CH_3)(CH_2CH_3)$, $CH(CH_2CH_2CH_3)$ and $CH(CH(CH_3)_2)$, preferably $CH_2$ or $CH(CH_3)$, substituted by a group $CONR^{12}C_{1-4}$alkyl$NR^aR^b$.

Preferred values of the group $NR^{20}R^{21}$ include:

$NHCH(CH_3)CONH_2$, $NHCH_2CONHCH_2CONH_2$, $NHCH_2CONHCH_3$, $N(CH_2CONH_2)_2$, $NHCH_2CONH(CH_2)_2OH$, $NHCH_2CONH_2$, $NHCH_2CON(CH_3)_2$, $N(CH_3)CONHCH_3$, $N(CH_3)CON(CH_3)_2$, $NHCH_2CONH(CH_2)_2OCH_3$, $N(CH_3)CH_2CONH(CH_2)_2OCH_3$,

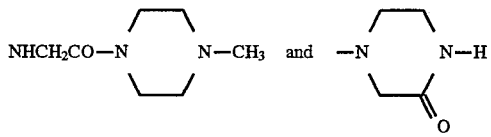

particularly $NHCH_2CONHCH_3$, $NHCH_2CON(CH_3)_2$, $N(CH_3)CONHCH_3$, $N(CH_3)CON(CH_3)_2$, $N(CH_3)CH_2CONH(CH_2)_2OCH_3$,

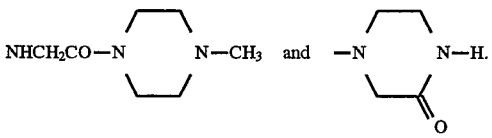

A further preferred value of the group $NR^{20}R^{21}$ is $NHCH_2CONH(CH_2)_2N(CH_3)_2$.

Preferably $R^{22}$ and $R^{23}$ each represent methyl or trifluoromethyl.

For use in medicine, the salts of the compounds of formula I will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, oxalic acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Preferred salts of the compounds of formula (I) include the tosylate, oxalate, bisoxalate, iodide and hydrochloride salts. Paricularly preferred are the hydrochloride and hydrobromide salts.

The present invention includes within its scope solvates of the compounds of formula (I) and salts thereof, for example, hydrates.

The compounds according to the invention have at least one asymmetric centre, and may accordingly exist both as enantiomers and as diastereoisomers. It is to be understood that all such isomers and mixtures thereof are encompassed within the scope of the present invention.

For compounds of the preferred sub-classes represented by formulae (Ib) and (Ic), (S) sterochemistry is preferred.

The present invention further provides pharmaceutical compositions comprising one or more compounds of formula (I) in association with a pharmaceutically acceptable carrier.

Preferably the compositions according to the invention are in unit dosage forms such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; neurodegenerative disorders such as dementia, including senile dementia of the Alzheimer type, Alzheimer's disease and Down's syndrome; demyelinating diseases such as MS and ALS and other neuropathological disorders such as peripheral neuropathy, for example diabetic and chemotherapy-induced neuropathy, and postherpetic and other neuralgias; respiratory diseases such as chronic obstrucutive airways disease, bronchopneumonia, bronchospasm and asthma; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as diserders associated with the neurona control of viscera such as ulcerative colitis, Crohn's disease and incontinence; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine. For example, the compounds of formula (I) may suitably be used in the treatment of disorders of the central nervous system such as anxiety, psychosis and schizophrenia; neurodegenerative disorders such as senile dementia of the Alzheimer type, Alzheimer's disease and Down's syndrome; respiratory diseases such as bronchospasm and asthma; inflammatory diseases such as inflammatory bowel disease, osteoarthritis and rheumatoid arthritis; adverse immunological reactions such as rejection of transplanted tissues; gastrointestinal (GI) disorders and diseases of the GI tract such as disorders associated with the neuronal control of viscera such as ulcerative colitis, Crohn's disease and incontinence; disorders of blood flow caused by vasodilation; and pain or nociception, for example, that attributable to or associated with any of the foregoing conditions or the transmission of pain in migraine.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and especially migraine.

The present invention further provides a compound of formula (I), DL-diphenylalanine benzyl ester hydrochloride salt, 2-benzamido-3,3-diphenylpropanoyl benzamide, or 2-benzamido-3-phenyl-3-benzyl-propanoyl benzamide, for use in therapy. According to a further or alternative aspect, the present invention provides a compound of formula (I), DL-diphenylalanine benzyl ester hydrochloride salt, 2-benzamido-3,3-diphenylpropanoyl benzamide, or 2-benzamido-3-phenyl-3-benzyl-propanoyl benzamide, for use in the manufacture of a medicament for the treatment of physiological disorders associated with an excess of tachykinins, especially substance P. The present invention also provides a method for the treatment or prevention of physiological disorders associated with an excess of tachykinins, especially substance P, which method comprises administration to a patient in need thereof of a tachykinin reducing amount of a compound of formula (I), DL-diphenylalanine benzyl ester hydrochloride salt, 2-benzamido-3,3-diphenylpropanoyl benzamide, or 2-benzamido-3-phenyl-3-benzyl-propanoyl benzamide, or a composition comprising a compound of formula (I), DL-diphenylalanine benzyl ester hydrochloride salt, 2-benzamido-3,3-diphenylpropanoyl benzamide, or 2-benzamido-3-phenyl-3-benzyl-propanoyl benzamide.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day. For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

According to one general process, (A), the compounds according to the invention wherein Z is O or S may be prepared by reaction of a compound of formula (II)

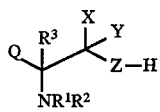

wherein Q, $R^1$, $R^2$, $R^3$, X and Y are defined as for formula (I) and Z is O or S, with a compound of formula $R^4$Hal, where $R^4$ is as defined for formula (I) and Hal is halo, such as bromo, chloro or iodo, in the presence of a base.

The reaction is conveniently carried out in a suitable organic solvent, such as ether, for example, tetrahydrofuran, suitably at ambient temperature.

Suitable bases of use in the reaction include alkali or alkaline earth metal hydrides, for example, sodium hydride.

According to a second general process, (B), compounds of formula (I) wherein Z is O or S, X and Y are H and $R^1$, $R^2$ and $R^3$ each represent H may be prepared from intermediates of formula (III)

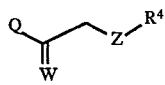

wherein Q and $R^4$ are as defined for formula (I), Z is O or S, and W represents a group NH or NOH, by reduction.

Suitable reducing agents of use in the reaction include, where W is NH, alkali metal borohydrides, such as, for example, sodium cyanoborohydride. Where W is NOH, suitable reducing agents include alkali metal hydrides, such as lithium aluminium hydride, borane, hydrogen in the presence of a catalyst, such as a nobel metal catalyst, for example rhodium, platinum or palladium, which may be supported, for example on carbon, dissolving metal reduction, for example using an alkali metal, such as sodium, in an alcohol, such as ethanol, or sodium amalgam.

The reaction is conveniently effected in a suitable organic solvent, such as an ether, for example, tetrahydrofuran, an alcohol, for example, ethanol or methanol, or a mixture of solvents. The solvents chosen will depend on the particular reducing agent used, and suitable solvents will be readily apparent to those skilled in the art.

The compounds of the invention wherein Z is a group $NR^7$ and X and Y together represent =O may be prepared from the compounds of formula (II) wherein Z is O and X and Y together represent =O by reaction with a compound of formula $HNR^7R^4$ in the presence of a coupling agent, such as dicyclohexylcarbodiimide.

The reaction is suitably effected in an aprotic organic solvent, such as dichloromethane or dimethylformamide, or a mixture thereof.

The compounds according to the invention wherein Z is $NR^7$ and X and Y are H may be prepared from the corresponding compounds of formula (I) wherein X and Y together represent =O, by reduction.

Suitable reducing agents of use in the reaction include borane and metal hydrides, such as lithium aluminium hydride. The reaction is conveniently effected in a suitable organic solvent, such as an ether, for example, tetrahydrofuran.

Compounds of formula (II) wherein Z is O and X and Y together represent a group =O may be prepared from intermediates of formula (VII)

wherein Q and $R^3$ are as above defined and Ph represents phenyl, by hydrolysis.

The reaction is conveniently effected by heating a solution of the compound of formula (VII) in concentrated hydrochloric acid at reflux.

Compounds of formula (II) wherein Z is S may be prepared from the corresponding compounds of formula (II) wherein Z is O by treating the latter compound with Lawesson's reagent or phosphorus pentasulphide in a suitable solvent, e.g. pyridine, at ambient or elevated temperature, suitably at the reflux temperature of the chosen solvent.

Compounds of formula (II) wherein X and Y represent H may be prepared from the corresponding compounds of formula (II) wherein X and Y together represent =O, by reduction.

Suitable reducing agents include metal hydrides, such as lithium aluminium hydride. The reaction is conveniently effected in a suitable organic solvent, such as ether, for example, tetrahydrofuran, suitably at elevated temperature, such as the reflux temperature of the solvent.

Conveniently, intermediates of formula (III) wherein W is NH (IIIA) are not isolated, but are generated in situ by reaction of a compound of formula (V)

wherein $R^4$ and Z are as defined for formula (III), by reaction with a metallated species of formula Q-M where Q is as defined for formula (I) and M is a metal, such as lithium, or a species MgHal, where Hal represents halo such as bromo, chloro or iodo. The metallated species Q-M is itself preferably generated in situ from a compound of formula Q-H, by conventional procedures, such as treatment with an organolithium reagent, for example n-butyl lithium.

Intermediates of formula (V) may be prepared by reaction of a compound of formula $R^4$-Hal, where Hal represents halo, such as chloro, bromo or iodo, with a compound $NCCH_2ZH$ in the presence of base, such as an alkali metal cabonate, for example potassium carbonate.

Compounds of formula (III) wherein W is NOH (IIIB) may be prepared from the corresponding ketones of formula (III) wherein W is O (IIIC) by reaction with hydroxylamine in the presence of a base. Suitably the hydroxylamine will be in the form of a salt, such as the hydrochloride salt.

Suitable bases of use in the reaction include teriary amines such as, for example, triethylamine.

Ketones of formula (IIIC) may be prepared from azides of formula (VI)

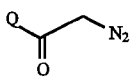

where Q is as defined for formula (I), by reaction with a compound of formula R⁴—Z—H, preferably in the presence of a suitable catalyst, such as rhodium acetate dimer.

The reaction is conveniently effected in a suitable organic solvent, such as a hydrocarbon, for example, benzene.

Compounds of formula (VI) may be prepared from acyl halides of formula QCOHal, where Q and Hal are as above defined, by treatment with diazomethane.

The diazomethane is employed as a solution in diethyl ether and the reaction is conducted at low temperature, such as about 0° C.

Acyl halides of formula QCOHal may be prepared from the corresponding carboxylic acids of formula $QCO_2H$ by conventional methods. Acids of formula $QCO_2H$ are known compounds or may be prepared from known compounds by conventional procedures, such as those set out in the accompanying examples, or methods analogous thereto.

Intermediates of formula (VII) may be prepared from compounds of formula (VIII)

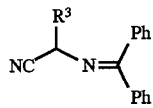

wherein $R^3$ is as defined for formula (I), by reaction with a compound of formula Q-Hal, where Q and Hal are as previously defined, in the presence of a base.

Suitable bases of use in the reaction include metal hydroxides, for example, sodium hydroxide. The reaction is conveniently effected in a mixture of water and a suitable organic solvent, such as a hydrocarbon, for example, toluene, in the presence of a phase transfer catalyst, such as benzyltrimethyl ammonium chloride.

Compounds of formula (VIII) are commercially available or may be prepared by procedures readily apparent to one skilled in the art.

Compounds of formula Q-Hal may be prepared according to the procedure described by E. J. Corey, *Tetrahedron Lett.*, 1972, 4339, or by other conventional procedures which will be readily apparent to those skilled in the art.

Compounds of formula (I) may also be prepared from other compounds of formula (I). Thus, for example, compounds of formula (I) wherein one or both of $R^1$ and $R^2$ represent hydrogen may be reacted with an optionally substituted alkylating or an acylating agent to produce compounds of formula (I) wherein one or both of $R^1$ and $R^2$ represent an optionally substituted alkyl or an acyl group. Suitable procedures are described in the accompanying examples, or will be readily apparent to one skilled in the art.

Conversely, compounds of formula (I) wherein one or both of $R^1$ and $R^2$ represent, for example, an acyl or a benzyl group, may be converted to compounds of formula (I) wherein one or both of $R^1$ and $R^2$ represent H by, for example, hydrolysis or catalytic hydrogenation. Suitable reagents and conditions are described in the accompanying examples, or will be readily apparent to one skilled in the art of organic chemistry.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantio-specific synthesis or by resolution. The novel compounds may, for example, be resolved into their component enantiomers by standard techniques, such as the formation of diastereomeric pairs by salt formation with an optically active acid, such as (–)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, for example, leucine methyl esters, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wutts, *Protective Groups in Organic Synthesis*, John Wiley & Sons, 1991. The protecting groups may be removed at a convenient subsequent stage using methods known from the art.

The following Examples illustrate the preparation of compounds according to the invention.

EXAMPLE 1

2-Ammoninm-1-((3,5-dimethylphenyl)methyloxy)-3,3-diphenylpronane tosylate salt a) To a solution of diphenylmethyleneiminoacetonitrile (44 g), benzyltrimethyl ammonium chloride (4.4 g) and sodium hydroxide (48.4 g) in toluene (40 ml) and water (90 ml) was added bromodiphenylmethane (149.4 g) at 0° C. After the solution had been stirred at room temperature for 5 h a mixture of water (200 ml), ethyl acetate (40 ml) and hexane (160 ml) was added. The solution was filtered and the residue washed with ethyl acetate/hexane and dried in vacuo to give 3,3-diphenyl-2-(diphenylmethyleneimino) proprionitrile 47.6 g. $^1$H NMR (360 MHz, $CDCl_3$) δ7.5–6.87 (20H, m, aryl), 4.8 (1H, d, J=8.85H), 4.69 (1H, d, J=9.2 Hz). An analytical sample was recrystallised from ethyl acetate/hexane mp=152°–153° C.

b) 3,3-Diphenyl-2-(Diphenylmethyleneimino)proprionitrile (Example 1a, 46.7 g, 0.12 Mol) was heated in a solution of 5.5M-hydrochloric acid (200 ml) at reflux for 48 h. The solid which crystallized from the cooled solution was removed by filtration, washed with diethyl ether and dried to give β,β-diphenylalanine hydrochloride 21 g. $^1$H NMR (250 MHz, DMSO $d_6$) δ8.6 (3H, vbs), 7.6–7.1 (10H, m), 4.8 (1H, d, J=10.4 Hz), 4.4 (1H, d, J=10.4 Hz).

c) To a solution of 1M-lithium aluminium hydride in diethyl ether (40 ml) was added β,β-diphenylalanine hydrochloride (3.70 g, Example 1b) over a period of 1 h. The solution was heated at reflux for 1 h, cooled to room temperature and to the solution was cautiously added 2M-sodium hydroxide (40 ml). After filtering the solution through Celite, the residue was washed with ethyl acetate and the organic phase of the combined filtrates was washed with water, saturate brine and dried ($MgSO_4$). The solid which formed on removal of the solvent in vacuo was washed with hexane to give 2-amino-3,3-diphenylpropan-1-ol 2.52 g, mp 107°–8° C. $^1$H NMR (360 MHz, $CDCl_3$) δ7.36–7.14 (10H, m), 3.79 (1H, d, J=10.5 Hz), 3.6 (1H, m), 3.57 (1H, dd, J=10.7 Hz and 3.3 Hz), 3.31 (1H, dd, J=10.7 Hz and 6.7 Hz), m/z ($CI^+$) 228 (M+H).

d) A solution of 2-amino-3,3-diphenylpropan-1-ol (2.3 g, Example 1c) and di-t-butyldicarbonate (2.65 g) in dichloromethane (25 ml) was stirred at room temperature for 1 h. The solid which formed on removal of the solvent was recrystallized from diethyl ether to give 2-t-butoxycarbonylamino-3,3-diphenylpropan-1-ol (2.85 g, mp 95°–96° C. $^1$H NMR (250 MHz, CDCl$_3$) δ7.34–7.15 (10H, m), 4.58 (1H, bd), 4.48 (1H, m), 4.1 (1H, d, J=10.6 Hz), 3.67 (1H, dd, J=11.13 Hz and 3.11 Hz), 3.5 (1H, dd, J=11.3 Hz and 4.45 Hz), 1.31 (9H, s).

e) To a solution of 2-t-butoxycarbonylamino-3,3-diphenylpropan-1-ol (1.0 g, Example 1d) in tetrahydrofuran (5 ml) and dimethylformamide (1 ml) was added sodium hydride (0.11 g, 80% suspension in oil) over 15 minutes. After an additional 10 minutes 3,5-dimethylbenzyl bromide (0.73 g) was added and the solution stirred at room temperature for 3 h. The solvent was removed in vacuo and the residue partitioned between ethyl acetate and water. After washing the organic phase with saturated brine and drying (MgSO$_4$), the solvent was removed in vacuo and the residue chromatographed on silica gel in ethyl acetate/hexane (1:10) to give 2-t-butoxycarbonylamino-1-((3,5-dimethylphenyl)methyloxy)-3,3-diphenylpropane 0.38 g. $^1$H NMR (360 MHz, CDCl$_3$) δ7.3–6.9 (13H, m), 4.7 (1H, bd), 4.6 (1H, bt), 4.43 (1H, d, J=16.7 Hz), 4.3 (2H, m), 3.4 (1H, dd), 3.2 (1H, dd, J=9.4 Hz and 2.82 Hz), 2.3 (6H, s), 1.3 (9H, s). m/z (CI$^+$) 446 (M+H).

f) A solution of 2-t-butoxycarbonyl-1-((3,5-dimethylphenyl)methyloxy)-3,3-diphenylpropane (0.38 g, Example 1e) in trifluoroacetic acid (10 ml) was evaporated after 10 minutes. A solution of the residue in ethyl acetate was washed with 10% aqueous sodium carbonate, water, saturated brine and dried (MgSO$_4$). Evaporation of the solvent in vacuo and chromatography of the residue on silica gel eluting with a mixture of chloroform:methanol:acetic acid (85:10:5) gave an oil (0.23 g) upon evaporation. To a solution of this residue in methanol, was added a solution of toluene sulfonic acid monohydrate (0.115 g) in methanol (5 ml). The solvent was removed in vacuo and the residue crystallized by addition of ethyl acetate/hexane to give 2-ammonium-1-((3,5-dimethylphenyl)methyloxy)-3,3-diphenylpropane tosylate salt mp 136°–137° C. $^1$H NMR (360 MHz, CDCl$_3$) 7.8 (3H, bs), 7.76 (2H, d, J=8.0 Hz), 7.42–7.14 (12H, m), 6.9 (1H, s), 6.8 (2H, s), 4.4–4.2 (3H, m), 4.12 (1H, bm), 3.62 (1H, dd, J=10 Hz and 2.72 Hz), 3.5 (1H, dd, J=10.5 Hz and 5.9 Hz), 2.36 (3H, s), 2.27 (6H, s). m/z (CI$^+$) 346 (M+H). Found C, 69.02; H, 6.60; N, 2.58. $C_{24}H_{27}NO.C_7H_8SO_3$. 1.25(H$_2$O) requires C, 69.04; H, 6.99; N, 2.59%.

EXAMPLE 2

2-Dimethylammonium-1-((3,5-dimethylphenyl)methyloxy)-3,3-diphenylpropane tosylate salt A solution of 2-t-butoxycarbonyl-((3,5-dimethylphenyl)methyloxy)-3,3-diphenylpropane (0.38 g, Example 1e) in trifluoroacetic acid (10 ml) was evaporated after 10 minutes. A solution of the residue in ethyl acetate was washed with 10% aqueous sodium carbonate, water, saturated brine and dried (MgSO$_4$). The solvent was removed in vacuo and to a cooled solution of the residue in methanol (10 ml) at 0° C. was added acetic acid (0.25 ml), sodium borohydride (0.106 g) and aqueous formaldehyde (0.167 ml, 38% w/v). After stirring the solution at room temperature for 1 h the solvent was removed in vacuo and the residue partitioned between ethyl acetate and 10% aqueous sodium carbonate. The organic phase was washed with water, saturated brine and dried (MgSO$_4$). Evaporation of the solvent and addition of 4-toluene sulfonic acid monohydrate (0:162 g) in ethanol gave after recrystallisation from ethyl acetate/hexane 2-dimethylammonium-1-((3,5-dimethylphenyl)methyloxy)-3,3-diphenylpropane tosylate salt mp 69°–75° C. $^1$H NMR (360 MHz, CDCl$_3$) δ7.76 (2H, d, J=8.1 Hz), 7.47–7.14 (13H, m), 6.92 (1H, s), 6.76 (2H, s), 4.58 (1H, d, J=11.0 Hz), 4.3 (1H, bd, J=10.8 Hz), 4.3 (1H, d, J=11.3 Hz), 4.1 (1H, d, J=11.6 Hz), 4.0 (1H, bd, J=10.2 Hz), 3.4 (1H, dd, J=11.8 Hz and 3.9 Hz), 3.0 (3H, d, J=4.8 Hz), 2.62 (3H, d, J=4.9 Hz), 2.34 (3H, s), 2.28 (6H, s). Found C, 70.87; H, 7.28; N, 2.42. $C_{26}H_{31}NO.C_7H_8SO_3.0.75(H_2O)$ requires C, 70.87; H, 7.30; N, 2.50%.

EXAMPLE 3

2-t-Butoxycarbonylamino-3,3-diphenylpropanoyl-(2-methoxyphenyl)methylamide a) A solution of β,β-diphenylalanine hydrochloride (2.5 g, 9.01 mmol), di-t-butyldicarbonate (3.0 g, 14.02 mmol) and triethylamine (2.6 ml) in dichloromethane (50 ml) was heated at reflux for 0.5 h. To the solution was added N,N-dimethylethylenediamine (0.49 ml) and the solution allowed to cool to room temperature. To the solution was added aqueous citric acid and the organic phase was washed with water, saturated brine and dried (MgSO$_4$). To the residue, obtained after removal of the solvent in vacuo, was added diethyl ether (30 ml) and dicyclohexylamine (1.63 g), to give after filtering and drying N-t-butoxycarbonyl-β,β-diphenylalanine dicyclohexylamine salt, 4.7 g mp 154°–154.5° C. $^1$H NMR (250 MHz, CDCl$_3$) δ7.4–7.0 (10H, m), 5.0 (1H, d, J=9.5 Hz), 4.7 (1H, dd), 4.5 (1H, d, J=7.05 Hz), 2.8 (2H, m), 1.9–1.5 (10H, m), 1.4–1.0 (19H, m). m/z (CI$^-$) 340 (M–H).

b) N-t-Butoxycarbonyl-β,β-diphenylalanine dicyclohexylamine (1.06 g) was liberated from its dicyclohexylamine salt by extraction into ethyl acetate from an aqueous citric acid solution, followed by washing (water and saturated brine) and drying (MgSO$_4$). The solvent was removed in vacuo and to a solution of the residue in dichloromethane (8 ml) and dimethylformamide (2 ml) was added 1-hydroxybenzotriazole (0.31 g) and dicyclohexylcarbodiimide (0.42 g). After the solution had been stirred for 15 minutes 2-methoxybenzylamine (0.334 g) was added and stirring continued for 16 h. The solution was filtered and the filtrate partially evaporated and dissolved in ethyl acetate and 10% aqueous sodium carbonate. After filtering the solution the two phases were separated and the organic phase washed further with 10% aqueous citric acid, water and saturated brine. After drying the solution (MgSO$_4$) the solvent was removed by evaporation and the residue recrystallized from hot methanol to give 2-t-butoxycarbonylamino-3,3-diphenylpropanoyl-(2-methoxyphenyl)methylamide 0.663 g, mp 197°–195.5° C. $^1$H NMR (250 MHz, CDCl$_3$) δ7.26–6.7 (14H, m), 6.0 (1H, bs), 4.99 (1H, bd), 4.80 (1H, t, J=9.6 Hz), 4.5 (1H, d, J=9.8 Hz), 4.26 (2H, d, J=5.9 Hz), 3.7 (3H, s), 1.3 (9H, s). m/z (CI$^+$) 461 (M+H). Found C, 73.14; H, 7.06; N, 6.16. $C_{28}H_{32}N_2O_4$ requires C, 73.03; H, 7.00; N, 6.08%.

EXAMPLE 4

2-Ammonium-3,3-diphenylpropanoyl-(2-methoxyphenyl)methylamide tosylate salt

A solution of 2-t-butoxycarbonylamino-3,3-diphenylpropanoyl-(2-methoxyphenyl)methylamide (0.454 g, Example 3b) in trifluoroacetic acid (10 ml) was stirred for 10 minutes then evaporated. To an ethanolic solution of the residue was added a solution of 4-toluene sulfonic acid (0.20 g) in ethanol. The solution was evaporated and the residue crystallized from ethyl acetate to give the title compound 0.29 g, mp 105° C. $^1$H NMR (360 MHz, DMSO d$_6$) 8.5 (1H, t), 8.3 (3H, bs), 7.5–7.2 (12H, m), 7.2 (1H, t), 7.1 (2H, d, J=7.5 Hz), 6.9 (1H, d), 6.6 (1H, t, J=7.9 Hz), 6.2 (1H, d, J=7.4 Hz), 4.78

(1H, bd), 4.3 (1H, d, J=11.3 Hz), 4.1 (1H, dd, J=15.8 and 6.3 Hz), 3.96 (1H, dd, J=15.8 Hz and 4.9 Hz), 3.73 (3H, s), 2.28 (3H, s). m/z (CI$^+$) 361 (M+H). Found C, 66.64; H, 6.03; N, 5.15.

$C_{23}H_{24}N_2O_2 \cdot C_7H_8SO_3 \cdot 0.5.(H_2O)$ requires C, 66.52; H, 6.14; N, 5.17%.

EXAMPLE 5

(3,5-Dimethylphenyl)methyl 2-ammonium-3,3-diphenylpropanoate tosylate salt a) N-t-Butoxycarbonyl-β,β-diphenylalanine dicyclohexylamine (2.5 g, Example 3a) was liberated from its dicyclohexylamine salt by extraction into ethyl acetate from an aqueous citric acid solution, followed by washing (water and saturated brine) and drying (MgSO$_4$). The solvent was removed in vacuo and to a solution of the residue in methanol (10 ml) was added a solution of caesium carbonate (0.78 g) in water. After the solution had been evaporated to dryness and evaporated repeatedly from a dimethylformamide solution, dimethylformamide (10 ml) and 3,5-dimethylbenzylbromide (1.43 g) were added. After stirring at room temperature for 16 h, the solvent was removed in vacuo and the residue partitioned between ethyl acetate and 10% aqueous sodium carbonate. The organic phase was washed further with water, saturated brine, dried (MgSO$_4$) and evaporated to dryness. The residue was recrystallized from ethyl acetate/hexane to give (3,5-dimethylphenyl)methyl 2-t-butoxycarbonylamino-3,3-diphenylpropanoate, 1.54 g, mp 123° C. $^1$H NMR (360 MHz, CDCl$_3$) δ7.40 (10H, m), 7.06 (1H, s), 6.84 (2H, s), 5.24 (1H, bt), 5.00 (3H, m), 4.50 (1H, bd), 2.40 (6H, s), 2.48 (9H, s). Found C, 74.95; H, 7.39; N, 3.09. $C_{28}H_{31}NO_4$ requires C, 75.31; H, 7.22; N, 3.14%.

b) (3,5-Dimethylphenyl)methyl 2-t-butoxycarbonylamino-3,3-diphenylpropanoate (1 g, Example 5a) was dissolved in trifluoroacetic acid (10 ml) for 10 minutes then evaporated to dryness. A solution of 4-toluene sulfonic acid (0.42) in ethanol was added and evaporated to dryness. On addition of ethyl acetate crystals formed which were removed by filtration and recrystallized from ethanol/diethyl ether to give (3,5-Dimethylphenyl)methyl 2-ammonium-3, 3-diphenyl propanoate tosylate salt 0.82 g, mp 116° C. $^1$H NMR (360 MHz, CDCl$_3$) δ8.18 (1H, bs), 7.62 (2H, d), 7.26 (2H, dt), 7.10 (10H, m), 6.84 (1H, s), 6.46 (2H,s), 4.86 (1H, bd), 4.62 (2H, s), 4.56 (2H, d), 2.38 (3H, s). m/z (CI$^+$) 360 (M+H). Found C, 69.78; H, 6.27; N, 2.64. $C_{24}H_{25}NO_2 \cdot C_7H_8SO_3$ requires C, 70.03; H, 6.26; N, 2.63%.

EXAMPLE 6

2-Methylammonium-1-((3,5-dimethylphenyl)methyloxy)-3, 3-diphenylpropane oxalate salt a) Sodium hydride (80% suspension in mineral oil, 0.089) was added to a cooled (0° C.) solution of 2-t-butoxycarbonylamino-1-((3,5-dimethylphenyl)methyloxy)-3,3-diphenylpropane (1 g, Example 1e) in dimethylformamide (7 ml). The solution was stirred at room temperature for 0.5 h followed by addition of methyl iodide (0.154 ml). After stirring the solution for a further 14 h water (100 ml) and ethyl acetate (30 ml) were added. The aqueous phase was washed further with ethyl acetate (2×30 ml) and the combined organic phases washed with saturated brine and dried (MgSO$_4$). Upon removal of the solvent in vacuo gave 2-(N-t-butoxycarbonyl-N-methyl)amino-1-((3,5-dimethylphenyl)methyloxy)-3,3-diphenylpropane 1.05 g as a colourless oil. This oil was dissolved in trifluoroacetic acid (5 ml) and after 0.75 h the solution was evaporated to dryness. The residue was partitioned between dichloromethane and 2M-NaOH. The organic phase was dried (K$_2$CO$_3$), evaporated in vacuo and the residue chromatographed in a mixture of CH$_2$Cl$_2$/CH$_3$OH/NH$_3$ (97:3:05). Addition of oxalic acid and recrystallisation of the resultant solid from diethyl ether/ethyl acetate/hexane gave 2-methylammonium-1-((3,5-dimethylphenyl)methyloxy)-3,-diphenylpropane oxalate salt mp.=176°–178° C. Found: C, 71.94; H, 6.79; N, 3.08; $C_{25}H_{29}NO \cdot C_2H_2O_4$ requires C, 72.14; H, 6.95; N, 3.12%.

EXAMPLE 7

2-Ethylammonium-1-((3,5-dimethylphenyl)methyloxy)-3, 3-diphenylpropane oxalate salt The title compound was prepared in an analogous manner to that described in Example 6, using ethyl iodide, mp=173°–177° C. Found: C, 71.51; H, 7.18; N, 3.0. $C_{26}H_{31}NO \cdot C_2H_2O_4 \cdot 0.4H_2O$ requires C, 71.44; H, 7.24; N, 2.98%.

EXAMPLE 8

2-Propylammonium-1-((3,5-dimethylphenyl)methyloxy)-3, 3-diphenylpropane oxalate salt The title compound was prepared in an analogous manner to that described in Example 6 using n-propyliodide, mp=116°–118° C. Found: C, 72.89; H, 7.29; N, 2.93. $C_{27}H_{33}NO \cdot C_2H_2O_4$ requires C, 72.93; H, 7.39; N, 2.93%.

EXAMPLE 9

2-Cyclopropylmethylammonium-1-((3,5-dimethylphenyl) methyloxy)-3,3-diphenylpropane tosylate salt The title compound was prepared in an analogous manner to that described in Example 6 using cyclopropylmethyl bromide, mp=123°–124° C. Found: C, 72.21; H, 7.15; N, 2.50. $C_{28}H_{33}NO \cdot C_7H_8SO_3 \cdot 0.5H_2O$ requires C, 72.38; H, 7.23; N, 2.41%.

EXAMPLE 10

2-Allylammonium-1-((3,5-dimethylphenyl)methyloxy)-3,3-diphenylpropane oxalate salt The title compound was prepared in an analogous manner to that described in Example 6 using allyl bromide. mp=123°–125° C. Found: C, 72.31; H, 7.06; N, 3.01. $C_{27}H_{31}NO \cdot C_2H_2O_4 \cdot 0.35(H_2O)$ requires C, 72.28; H, 7.05; N, 2.91%.

EXAMPLE 11

2-Benzylammonium-1-((3,5-dimethylphenyl)methyloxy)-3, 3-diphenyl propane

The title compound was prepared in an analogous manner to that described in Example 6 using benzylbromide, mp=117°–119° C. Found: C, 79.39; H, 6.85; N, 2.95. $C_{31}H_{33}NO \cdot 0.55(C_2H_2O_4)$ requires C, 79.47; H, 7.08; N, 2.88%.

EXAMPLE 12

1-((3,5-Dimethylphenyl)methyloxy)-3,3-diphenyl-2-(N,N, N-trimethylammonium)propane iodide salt Methyl iodide (0.7 ml) was added to a solution of 2-dimethylamino-1-((3,5-dimethylphenyl)methyloxy)-3,3-diphenylpropane (1.04 g; Example 2, liberated from the salt by partitioning between CH$_2$Cl$_2$ and 2M-NaOH, drying (K$_2$CO$_3$) and evaporating the organic phase) in tetrahydrofuran (10 ml) under an atmosphere of nitrogen. After the solution had been stirred at 60° C. for 23 h, the solvent was removed in vacuo and diethyl ether added to give the title compound mp=91°–92° C. as a hygroscopic colourless solid. Found: C, 62.32; H, 6.66; N, 2.69. $C_{27}H_{34}NO I.0.25H_2O$ requires C, 62.37; H, 6.69; N, 2.69%.

EXAMPLE 13

3,3-Diphenyl-1-((3,5-dimethylphenyl)methyloxy)-2-(1-pyrrolidinium)propane tosylate salt 1,4-Diiodobutane (0.54 ml) was added to a solution of 2-amino-1-((3,5-dimethylphenyl)methyloxy)-3,3-diphenylpropane (0.9 g; Example 1, liberated from the salt by partitioning between $CH_2Cl_2$ and 2M-NaOH, drying ($K_2CO_3$) and evaporating the organic phase) in ethanol (25 ml) containing potassium carbonate (4.0 g) and sodium acetate (0.7 g). The mixture was heated at reflux for 17 h, cooled to room temperature and the solvent removed in vacuo. A solution of the residue in $CH_2Cl_2$ was washed with 1M-NaOH (60 ml), brine and dried ($K_2CO_3$). After removal of the solvent by evaporation in vacuo the residue was chromatographed on silica (eluting with hexane:ethyl acetate:triethylamine 95:5:1) and tosic acid added to give the title compound mp=162°–165° C. Found: C, 73.49; H, 7.25; N, 2.43. $C_{28}H_{33}NO \cdot C_7H_8SO_3$ requires C, 73.52; H, 7.23; N, 2.45%.

EXAMPLE 14

3,3-Diphenyl-1-((3,5-dimethylphenyl)methyloxy)-2-(piperidin-1-yl)propane hydrochloride salt The title compound was prepared in an analogous manner to Example 13 using 1,5-diiodopentane, mp=186°–188° C. Found: C, 76.54; H, 7.91; N, 3.15. $C_{29}H_{35}NO \cdot HCl \cdot 0.25(H_2O)$ requires C, 76.63; H, 8.09; N, 3.08%.

EXAMPLE 15

3,3-Diphenyl-1-((3,5-dimethylphenyl)methyloxy)-2-(4-morpholino)propane

2-Chloroethyl ether (10 g) and sodium iodide (26 g) were refluxed in acetone (50 ml) for 16 h. Diethyl ether and water were added to the solution and the organic phase dried ($MgSO_4$) and evaporated in vacuo. The residue was chromatographed on silica (eluting with 3% ethyl acetate in hexanes) to give 2-iodoethyl ether (4 g). The title compound was prepared in an analogous manner to Example 13 using the 2-iodoethyl ether, mp 81°–83° C. Found: C, 80.32; H, 7.99; N, 3.42. $C_{28}H_{33}NO_2 \cdot 0.2H_2O$ requires C, 80.23; H, 8.03; N, 3.34%.

EXAMPLE 16

2-Ammonium-1-((3,5-bis(trifluoromethyl)phenyl)methyloxy)-3,3-diphenylpropane oxalate salt
1) Method A The title compound was prepared in an analogous manner to that described in Example 1e,f using bistrifluoromethylbenzyl bromide, mp=118°–121° C. Found: C, 52.05; H, 4.12; N, 2.57. $C_{22}H_{21}N_1O_1F_6 \cdot 1.5 (C_2H_2O_4) \cdot 0.5(H_2O)$ requires C, 52.36; H, 4.39; N, 2.44%.
2) Method B a) To a solution of cyanohydrin (70% in water, 20 ml) and powdered $K_2CO_3$ (90.7 g) in ethyl acetate (250 ml) was added 3,5-bis(trifluoromethyl)benzyl bromide (40.3 g). The solution was stirred at room temperature for 15 minutes then was heated to reflux for 2.5 hours. After cooling to room temperature water (500 ml) and ethyl acetate (500 ml) were added and the organic phase washed with saturated brine (2 times) and dried ($MgSO_4$). After removal of the solvent in vacuo the residual oil was distilled under reduced pressure through a 3" vigreux column $bp_{1.8}$=92°–108° to give ((3,5-bis(trifluoromethyl)phenyl)methyloxy)acetonitrile. $^1$H NMR (250 MHz, $CDCl_3$) δ7.86 (1H, s), 7.82 (2H, s), 4.85 (2H, s), 4.40 (2H, s).

b) To a cooled (–80° C.) solution of ((3,5-bis(trifluoromethyl)phenyl)methyloxy)acetonitrile (Example 18a, Method B, 1.2 g) in tetrahydrofuran (5 ml) was added boron trifluoride etherate (0.52 ml) and 0.42M lithio diphenylmethane (15 ml, prepared by addition of 2.5M n-butyl lithium (10 ml) to a cooled (–80° C.) solution of diphenylmethane (4.2 g) in tetrahydrofuran (50 ml), followed by warming to room temperature for 1 h). The solution was warmed to room temperature and after 1 hour glacial acetic acid (0.5 ml) and methanol (10 ml) were added followed by addition of sodium cyanoborohydride (0.8 g). After 15 minutes solid $Na_2CO_3$, water and ethyl acetate were added and the organic phase washed with water, saturated brine and dried ($MgSO_4$). After removal of the solvent in vacuo the residue was purified by chromatography on silica gel (washing the column with ethyl acetate/petroleum ether (1:1) and eluting the product with ethyl acetate). The product was evaporated to dryness and 1M HCl in methanol added and re-evaporated. The residual crystalline solid was washed with diethyl ether to give 2-ammonium-1-((3,5-bis(trifluoromethyl)phenyl)methyloxy)-3,3-diphenylpropane chloride, mp=210°–214° C. $^1$H NMR (250 MHz, DMSO-$d_6$) δ8.15 (3H, vbs), 8.06 (2H, s), 8.03 (1H, s), 7.55°–7.14 (10H, m), 4.67 (1H, d, J=13 Hz), 4.52 (2H, d+m), 4.22 (1H, d, J=12 Hz), 3.66 (1H, dd), 3.4 (1H, dd, J=10.5 Hz, 4.9 Hz).

EXAMPLE 17

2-Dimethylammonium-1-((3,5-bis-trifluoromethylphenyl)methyloxy)-3,3-diphenylpropane The title compound was prepared from 2-ammonium-1-((3,5-bis-trifluoromethylphenyl)methyloxy)-3,3-diphenylpropane (Example 16) using the procedure described in Example 2, mp=144°–145° C. Found: C, 60.69; H, 5.05; N, 2.16. $C_{26}H_{25}NOF_6 \cdot C_7H_8SO_3$ requires C, 60.63; H, 5.08; N, 2.14%.

EXAMPLE 18

2-Ammouinm-1-((3,5-dichlorophenyl)methyloxy)-3,3-diphenylpropane tosylate salt

The title compound was prepared in an analogous manner to that described in Example 1e,f using 3,5-dichlorobenzyl bromide, mp=156°14 157° C. Found: C, 62.37; H, 5.21; N, 2.52. $C_{22}H_{21}NOCl_2 \cdot C_7H_8SO_3$ requires C, 62.36; H, 5.23; N, 2.51%.

EXAMPLE 19

2-Ammonium-1-((3-chlorophenyl)methyloxy)-3,3-diphenylpropane tosylate salt

The title compound was prepared in an analogous manner to that described in Example 1e,f using 3-chlorobenzyl bromide, mp=168°–169° C. Found: C, 65.89; H, 5.69; N, 2.70. $C_{22}H_{22}NOCl \cdot C_7H_8SO_3 \cdot 0.25(H_2O)$ requires C, 65.89; H, 5.82; N, 2.65%.

EXAMPLE 20

2-(N-(Carbomethoxymethyl)ammonium)-1-((3,5-dimethylphenyl)methyloxy)-3,3-diphenylpropane tosylate salt A solution of 2-amino-1-((3,5-dimethylphenyl)methyloxy)-3,3-diphenylpropane (3.44 g, liberated from the tosylate salt (Example 1) by partitioning between ethyl acetate and 10% $Na_2CO_3$ solution), methyl bromoacetate (0.98 ml) and triethylamine (1.39 ml) in tetrahydrofuran (50 ml) was heated to reflux for 16 h. The solution was cooled, concentrated in vacuo and partitioned between ethyl acetate and water. The organic phase was washed with water, saturated brine and dried ($MgSO_4$). After evaporation the residue was chromatographed on silica gel eluting successively with a mixture of 5% to 25% ethyl acetate in petroleum ether (bp=60°–80° C.). The fractions containing the desired product were evaporated and a solution of 4-toluenesulfonic acid in ethanol added, evaporated to dryness and crystallised by addition of diethyl ether to give the title compound, mp=99°–101° C. $^1$H NMR (DMSO-$d_6$, 360 MHz) 7.56 (2H, d, J=7.4 Hz), 7.49 (2H, d, J=8.04 Hz), 7.36 (4H, t), 7.296 (3H, t), 7.20 (1H, dd), 7.1 (2H, d, J=7.73 Hz), 6.89 (1H, bs), 6.80 (2H, bs), 4.55 (1H, vbd), 4.37 (2H, d), 4.2 (1H, d, J=12 Hz), 3.8 (2H, dd), 3.7 (3H, s), 3.6 (1H, d, J=9.6 Hz), 3.4 (1H, dd, J=9.6, 4.3 Hz), 2.29 (3H, s), 2.23 (6H, s). Found: C, 69.35; H, 6.74; N, 2.35. $C_{27}H_{31}NO_3.C_7H_9SO_3$ requires: C, 69.24; H, 6.66; N, 2.37%.

EXAMPLE 21

2-(((Carboxamido)methyl)amino)-1-((3,5-dimethylphenyl)methyloxy)-3,3-diphenylpropane A solution of the methyl ester (Example 20, 1 g) in methanol (30 ml) was saturated with ammonia at 0° C. The flask was sealed and stored at 5° C. for 72 h. The solvent was removed in vacuo and the residue chromatographed on silica gel eluting with increasing concentrations of ethyl acetate in petroleum ether (0 to 50%). Fractions containing the desired product were evaporated in vacuo and the residue recrystallised from hot diethyl ether to give the title compound 624 mg, mp=72°–74° C. $^1$H NMR (CDCl$_3$, 360 MHz) δ7.36–7.16 (10H, m, aryl), 6.91 (1H, s), 6.85 (2H, s), 5.01 (1H, bs), 4.28 (2H, s), 4.08 (1H, d, J=10.8 Hz), 3.50 (1H, dd, J=9.8 Hz and 2.71 Hz), 3.4 (1H, dr, J=10.7 Hz and 3.4 Hz), 3.2 (1H, dd, J=9.8 Hz and 3.9 Hz), 3.19 (1H, d, J=2.5 Hz), 2.30 (6H, s). Found: C, 77.82; H, 7.53; N, 6.96. $C_{26}H_{30}N_2O_2$ requires C, 77.68; H, 7.51; N, 6.95%.

EXAMPLE 22

2-(N-(2-Hydroxyethyl)ammonium)-1-((3,5-dimethylphenyl)methyloxy)-3,3-diphenylpropane oxalate salt To a cooled (0° C.) solution of the methyl ester (Example 20, 0.52 g) in tetrahydrofuran (20 ml) was added a solution of lithium aluminium hydride (1M in tetrahydrofuran, 2.4 ml). After 10 minutes to the solution was cautiously added water (2 ml) and 2M sodium hydroxide solution (2 ml) and ethyl acetate. The suspension was filtered through Hyflo and the resultant organic phase evaporated to dryness and chromatographed on silica gel eluting sequentially with (50% to 100%) ethyl acetate in petroleum ether (bp 60°–80° C.) followed by 2% methanol in ethyl acetate. The resultant purified product was crystallised from diethyl ether as the oxalate salt to give the title compound, mp=150°–154° C. Found: C, 69.38; H, 6.94; N, 2.89. $C_{26}H_3NO_2.C_2H_2O_4.0.25(H_2O)$ requires C, 69.47; H, 6.97; N, 2.89%.

EXAMPLE 23

2-Formamido-1-((3,5-dimethylphenyl)methyloxy)-3,3-diphenylpronane

To a solution of 2-amino-1-((3,5-dimethylphenyl)methyloxy)-3,3-diphenylpropane (1.2 g, liberated from the tosylate salt (Example 1) by partitioning between ethyl acetate and 10% $Na_2CO_3$ solution) in tetrahydrofuran (5 ml) was added a cooled solution formed by heating a mixture of formic acid (3 ml) in acetic anhydride (60 ml) for 20 minutes at 60° C. The solution was stirred at room temperature for 16 h then evaporated to dryness and the residue chromatographed on silica gel eluting with a mixture of ethyl acetate in hexane. Addition of hexane gave the title compound as a solid, mp=74°–76° C. Found: C, 80.13; H, 7.47; N, 3.81. $C_{25}H_{27}NO_2$ requires C, 80.39; H, 7.29; N, 3.75%.

Using a procedure analogous to Example 1e,f and the appropriate benzylbromide were the following Examples similarly prepared.

EXAMPLE 24

2-Ammonium-1-((3-nitrophenyl)methyloxy)-3,3-diphenylpropane oxalate salt

Mp=75°–85° C. Found: C, 62.93; H, 5.49; N, 6.11. $C_{22}H_{22}N_2O_3.C_2H_2O_4.0.25(H_2O)$ requires C, 63.08; H, 5.40; N, 6.13%.

EXAMPLE 25

2-Ammonium-1-benzyloxy-3,3-diphenylpropane oxalate salt

Mp=147°–150° C. Found: C, 69.90; H, 6.25; N, 3.43. $C_{22}H_{23}NO.C_2H_2O_4$ requires C, 69.82; H, 6.25; N, 3.39%.

EXAMPLE 26

2-Ammonium-2-((3-iodophenyl)methyloxy)-3,3-diphenylpropane oxalate salt

Mp=152°–154° C. Found: C, 54.23; H, 4.49; N, 2.67. $C_{22}H_{22}NOI.C_2H_2O_4$ requires C, 54.05; H, 4.54; N, 2.63%.

EXAMPLE 27

2-Ammonium-1-((3,5-dimethoxyphenyl)methyloxy-3,3-diphenylpropane oxalate salt

Mp=101°–102° C. Found: C, 65.16; H, 6.24; N, 2.95. $C_{24}H_{27}NO_3.C_2H_2O_4.0.625(H_2O)$ requires C, 65.22; H, 6.36; N, 2.92%.

EXAMPLE 28

2-Ammonium-1-((2,5-dimethylphenyl)methyloxy)-3,3-diphenylpropane oxalate salt

Mp=105°–108° C. Found: C, 68.07; H, 6.53; N, 3.09. $C_{24}H_{27}NO.1.4(C_2H_2O_4)$ requires C, 68.26; H, 6.37; N, 2.97%.

EXAMPLE 29

2-Ammoninm-1-((3-cyanophenyl)methyloxy)-3,3-diphenylpropane oxalate salt

Mp=121°–124° C. Found: C, 69.15; H, 5.58; N, 6.47. $C_{23}H_{22}N_2O.C_2H_2O_4$ requires C, 69.43; H, 5.59; N, 6.48%.

EXAMPLE 30

1-((3,5-Bis(trifluoromethyl)phenyl)methyloxy)-2-((carboxamido)methyl)ammoninm)-3,3-diphenylpropane oxalate salt The title compound was prepared from 2-ammonium-1-((3,5-bis(trifluoromethyl)phenyl)methyloxy)-3,3-diphenylpropane oxalate salt (Example 16) using an analogous procedure to that described in Example 20 and Example 21, mp=135°–139° C.

Found: C, 55.33; H, 4.45; N, 4.74. $C_{26}H_{24}F_6N_2O_2.C_2H_2O_4$ requires C, 55.58; H, 4.42; N, 4.63%.

EXAMPLE 31

2-Ammonium-1-((3-bromophenyl)methyloxy)-3,3-diphenylpropane oxalate salt

The title compound was prepared by an analogous manner to that described in Example 1e,f using 3-bromobenzyl bromide. Mp=130°–134° C. Found: C, 58.88; H, 5.07; N, 2.92; $C_{22}H_{22}BrNO.C_2H_2O_4$ requires C, 59.27; H, 4.97; N, 2.88%.

EXAMPLE 32

2-Ammonium-1-((3,5-dibromophenyl)methyloxy)-3,3-diphenylpropane oxalate salt

The title compound was prepared by an analogous manner to that described in Example 1e,f using 3,5-dibromobenzyl bromide. Mp=194°–195° C. Found: C, 52.31; H, 4.25; N, 2.67; $C_{22}H_{21}Br_2NO.0.7$ $(C_2H_2O_4)$ requires C, 52.22; H, 4.19; N, 2.60%.

EXAMPLE 33

2-Ammonium-1-((3-bromo-5-methylphenyl)methyloxy)-3,3-diphenylpropane oxalate salt

The title compound was prepared by an analogous manner to that described in Example 1e,f using 3-bromo-5-methyl-benzyl bromide. Mp=137°–138° C. Found: C, 59.57; H, 5.10; N, 2.74; $C_{23}H_{24}BrNO.C_2H_2O_4.0.2(H_2O)$ requires C, 59.57; H, 5.28; N, 2.78%.

EXAMPLE 34

1-((3,5-Bis(trifluoromethyl)phenyl)methyloxy)-2-(cyanomethyl)amino-3,3-diphenylpropane

2-Amino-1-((bis(trifluoromethyl)phenyl)methyloxy)-3,3-diphenylpropane (0.8 g, liberated from the oxalate salt (Example 16) by partitioning between 10% aqueous $Na_2CO_3$ and ethyl acetate) was dissolved in tetrahydrofuran (30 ml) together with triethylamine (0.492 ml) and bromoacetonitrile (0.246 ml), and the mixture heated at reflux for 4 h. After the solvent had been removed in vacuo the residue was chromategraphed on silica gel eluting with mixtures of 5% to 50% of ethyl acetate in petroleum ether (bp 60°–80° C.). The product was evaporated in vacuo to an oil which crystallised on standing to give the title compound, mp=78°–80° C. Found: C, 63.67; H, 4.60; N, 5.67; $C_{26}H_{22}N_2OF_6$ requires C, 63.41; H, 4.50; N, 5.68%. m/e (CI$^+$)=493 (M+H).

EXAMPLE 35

2-((2-Ammonium)ethylammonium)-1-((3,5-bis(trifluoromethyl)phenyl)methyloxy)-3,3-diphenylpropane bis oxalate salt

To a solution of the aminonitrile (Example 34, 0.32 g) in tetrahydrofuran (20 ml) was added a solution of 1M-borane in tetrahydrofuran (2 ml) and the mixture heated at reflux for 18 h. Ethyl acetate and 1M-HCl were added to the cooled solution and the organic phase was washed further with saturated brine and dried (MgSO$_4$). After removal of the solvent in vacuo the residue was chromatographed on silica gel eluting with 1% ammonia solution (SG=0.88) in $CH_2Cl_2$ (v/v) containing 1%, 2% and 5% methanol. The product, isolated as an oil after removal of the solvent in vacuo was crystallized by formation of the bis oxalate salt in diethyl ether. Recrystallization from ethanol/diethyl ether gave the title compound as a hygroscopic solid mp=125°–135° C. Found: C, 51.54; H, 4.67; N, 4.04; $C_{26}H_{26}F_6N_2O.2.0$ $(C_2H_2O_4)$ requires C, 51.88; H, 4.64; N, 4.03%.

EXAMPLE 36

2-(N-((Carboxamido)methyl)-N-methyl)ammonium-1-((3,5-dimethylphenyl)methyloxy)-3,3-diphenyl propane oxalate salt

To a solution of the amino ester (Example 20, 0.68 g, liberated from the tosylate salt by partitioning between 10% $Na_2CO_3$ and ethyl acetate) in dimethyl formamide (20 ml) was added sodium hydride (80% suspension in oil, 0.064 g). After the effervescence had ceased, methyl iodide (0.2 ml) was added and the solution stirred under an atmosphere of nitrogen for 16 h. The product was partitioned between ethyl acetate and water, and the organic phase dried (MgSO$_4$) and evaporated in vacuo. The resultant oil was chromatographed on silica gel eluting with a mixture of ethyl acetate (5% to 25%) in petroleum ether (BP=60°–80° C.) to give 2-(N-(carbomethoxy)methyl-N-methyl)amino-1-((3,5-dimethylphenyl)methyloxy)-3,3-diphenylpropane. The methyl ester above was dissolved in methanol (20 ml), saturated with ammonia gas (0° C.) and the solution kept at 5° C. in a sealed container for 72 h. The solvent was removed in vacuo and the residual oil chromatographed on silica gel (eluting with 20% ethyl acetate in petroleum ether (BP=60°–80° C.)). Oxalic acid was added and the resultant salt crystallized from ethyl acetate/petroleum ether to yield the title compound mp=108°–111° C. Found: C, 62.88; H, 6.64; N,.4.83; $C_{27}H_{32}N_2O_2.1.5(C_2H_2O_4).H_2O$ requires C, 63.25; H, 6.54; N, 4.91%. m/e (CI$^+$)=417 (M+H), (CI$^-$)=415 (M–H).

EXAMPLE 37

2-((N-Methyl)acetamido)-1-((3,5-dimethyl)phenyl)methyloxy)-3,3-diphenylpropane

2-(N-t-butoxycarbonyl-N-methyl)amino-1-((3,5-dimethylphenyl)methyloxy)-3,3-diphenylpropane (Example 6, 3.5 g) was dissolved in trifluoroacetic acid (40 ml). After 30 minutes the solvent was removed in vacuo and the residue partitioned between dichloromethane and 2M-sodium hydroxide solution (100 ml). The organic phase was washed with 2M-NaOH (100 ml), saturated brine, dried (MgSO$_4$) and evaporated in vacuo to give an oil (2.21 g). A portion of this oil (1.0 g) was dissolved in pyridine (0.34 ml) and acetic anhydride (0.4 ml) in $CH_2Cl_2$ (10 ml). After the solution had been stirred at room temperature for 16 hours, ethyl acetate (100 ml) was added and the solution washed with water (3×100 ml), saturated brine and dried (MgSO$_4$). The residue after removal of the solvent in vacuo was purified on silica gel and evaporated to an oil which crystallised on standing to give the title compound, mp=80°–83° C. Found: C, 81.03; H, 7.90; N, 3.80; $C_{27}H_{31}NO_2$ requires C, 80.76; H, 7.78; N, 3.49%. m/e (CI$^+$=402 (M+H).

EXAMPLE 38

2-Acetamido-1-(((3,5-dimethyl)phenyl)methyloxy)-3,3-diphenylpronane

The title compound was prepared from 2-amino-1-(((3,5-dimethyl)phenyl)methyloxy)-3,3-diphenylpropane by acetylation as described in Example 37, mp=148° C. Found: C, 80.17; H, 7.61; N, 3:60; $C_{26}H_{29}NO_2$ requires C, 80.21; H, 7.56; N, 3.59%, m/e (CI$^+$)=388 (M+H).

EXAMPLE 39

2-(((N-Methyl)benzamido)-1-((3,5-dimethyl)phenyl)methyloxy)-3,3-diphenylpropane

The title compound was prepared from 2-(N-t-butoxycarbonyl-N-methyl)amino-1-((3,5-dimethylphenyl)methyloxy)-3,3-diphenylpropane (Example 6) in an analogous manner to that described in Example 37 using benzoyl chloride, mp=89°–91° C. Found: C, 83.07; H, 7.16; N, 3.09, $C_{32}H_{33}NO_2$ requires C, 82.90; H, 7.17; N, 3.02%. m/e (CI$^+$=464 (M+H).

EXAMPLE 40

2-Benzamido-1-(((3,5-dimethyl)phenyl)methyloxy)3,3-diphenylpropane

The title compound was-prepared from 2-amino-2-(((3,5-dimethyl)phenyl)methyloxy)3,3-diphenylpropane (Example 1) by benzoylation as described in Example 39, mp=128°–129° C., m/e (CI⁺)=450 (M+H). Found: C, 79.62; H, 6.87; N, 3.00, $C_{31}H_{31}NO_2.H_2O$ requires C, 79.63; H, 7.11; N, 3.02%.

EXAMPLE 41

1-((3',5'-Bis(trifluoromethyl)phenyl)methyloxy)-2-((1-(carboxamido)ethyl)ammonium)-3,3-diphenylpropane oxalate salt The title compound was prepared from 2-ammonium-1-((3,5-bis(trifluoromethyl)phenyl)methyloxy-3,3-diphenylpropane oxalate salt (Example 16) using an analogous procedure to that described in Example 20 with methyl 2-bromoproprionate to give a mixture of isomers (approximately 1:1) which were separated by chromatography on silica gel. The separated diastereomers were treated with ammonia in an analogous manner to that described in Example 21 and crystallised by addition of oxalic acid to give the title compound (diastereomer A), mp 108°–110° C. Found: C, 55.02; H, 4.51; N, 4.48; $C_{27}H_{26}F_6N_2O_2.C_2H_2O_4.H_2O$ requires C, 55.06; H, 4.78; N, 4.43%; ¹H NMR (360 MHz, DMSO d₆) 1.02 (3H, d, J=6.85 Hz, $CH_3$) and the title compound (diastereomer B) mp=166°–168° C., Found: C, 56.07; H, 4.45; N, 4.38; $C_{27}H_{26}F_6N_2O_2.C_2H_2O_4.0.4(H_2O)$ requires C, 56.02; H, 4.67; N, 4.50%; ¹H NMR (360 MHz, DMSO d₆) 1.15 (3H, d, J=6.8 Hz, $CH_3$).

EXAMPLE 42

N-(1-((3',5'-Bis(trifluoromethyl)phenyl)methyloxy)-3,3-diphenylprop-2-yl)-N'-methyl urea To a solution of 2-amino-1-((3',5'-bis(trifluoromethyl)phenyl)methyloxy)-2,2-diphenylpropane (1.0 g, Example 16; liberated from the oxalate salt by extraction into ethyl acetate from a 10% sodium bicarbonate solution) in dichloromethane was added triethylamine (5 ml) and methyl isocyanate (2 ml). The solution was heated at 40° C. for 16 h and at reflux for a further 4 h. After the solvent had been removed by evaporation, the residue was purified by chromatography on silica gel to give the title compound, mp 128°–130° C. Found: C, 61.19; H, 4.71; N, 5.66; $C_{26}H_{24}N_2O_2F_6.0.75(H_2O)$ requires C, 61.17; H, 4.74; N, 5.48%. m/z (CI⁺)=511 (M+H), (CI⁻)=510 (M).

EXAMPLE 43

N-(1-((3',5'-Bis(trifluoromethyl)phenyl)methyloxy)-3,3-diphenylprop-2-yl)-N'-phenylurea The title compound was prepared in an analogous manner to that described in Example 42 using phenylisocyanate, mp 124°–126° C., m/e (CI⁺)=573 (M+H), (CI⁻)=571 (M–H). Found: C, 65.03; H, 4.57; N, 4.89; $C_{31}H_{26}N_2O_2F_6$ requires C, 64.79; H, 4.74; N, 4.76%.

EXAMPLE 44

N-(1-((3',5'-Bis(trifluoromethyl)phenyl)methyloxy)-3,3-diphenylprop-2-yl)glycine To a solution of 1-((3',5'-Bis(trifluoromethyl)phenyl)methyloxy)-2-(N-((carbomethoxy)methyl)amino)-3,3-diphenylpropane (prepared as intermediate, Example 30, 2.38 g) in tetrahydrofuran (25 ml) was added 1M-potassium hydroxide solution (25 ml) and the mixture heated to reflux for 16 hours. The solvent was removed by evaporation and 1M-hydrochloric acid was added to an aqueous solution of the residue until pH=2. The gum which formed was recrystallised from aqueous ethanol to give the title compound mp 116°–119° C.; m/e (CI⁺) 512 (M+H), (CI⁻) 511 (M).

Found: C, 60.06; H, 4.55; N, 2.66; $C_{26}H_{23}NO_3F_6.0.5(H_2O)$ reqires C, 60.00; H, 4.64; N, 2.69%.

EXAMPLE 45

N-(1-(((3',5'-Dimethyl)phenyl)methyloxy)-3,3-diphenylprop-2-yl)glycine

The title compound was prepared from 2-(N-carbomethoxymethyl)amino-1-((3',5'-diphenyl)methyloxy)-3,3-diphenylpropane (Example 20) using a procedure analogous to that described in Example 44, mp 85°–87° C., m/e (CI⁺) 404 (M+H), (CI⁻) 402 (M–H). Found: C, 75.20; H, 7.35; N, 3.37; $C_{26}H_{29}NO_3.0.65(H_2O)$ requires C, 75.15; H, 7.20; N, 3.36%.

EXAMPLE 46

N-(1-(((3',5'-Dimethyl)phenyl)methyloxy)-3,3-diphenylprop-2-yl)glycylglycine amide To a solution of the amino acid (Example 45, 0.225 g), glycinamide hydrochloride (0.062 g), 1-hydroxybenzotriazole (0.084 g) and triethylamine (0.153 ml) in dichloromethane (20 ml) was added 1-(3-dimethylaminopropyl)-3-ethylcarbodiimide (0.105 g). After stirring the solution for 16 hours water was added and the organic phase dried ($MgSO_4$). After evaporation in vacuo and column chromatography on silica gel (50% to 100% ethyl acetate in petroleum ether, followed by 1% to 5% methanol in ethyl acetate) to give the title compound, mp 116°–117° C.; m/e (CI⁺)=460 (M+H), (CI⁻)=458 (M–H). Found: C, 71.38; H, 7.04; N, 8.81; $C_{28}H_{33}N_3O_3.0.6(H_2O)$ requires C, 71.49; H, 7.32; N, 8.93%.

EXAMPLE 47

N-(1-(((3',5'-Dimethyl)phenyl)methyloxy)-3,3-diphenylprop-2-yl)glycylbenzamide oxalate salt Using a coupling procedure analogous to that described in Example 46 between the amino acid (Example 45) and benzylamine gave the title compound, mp 44°–47° C., m/e (CI⁺)=493 (M+H), (CI⁻)=491 (M+H). Found: C, 70.94; H, 6.42; N, 4.60; $C_{33}H_{36}N_2O_2.C_2H_2O_4.0.5(H_2O)$ requires C, 71.04; H, 6.64; N, 4.73%.

EXAMPLE 48

N-(1-((3',5'-Bis(trifluoromethyl)phenyl)methyloxy)-3,3-diphenylprop-2-yl)glycine dimethylamide hydrochloride salt A solution of 1-((3',5'-bis(trifluoromethyl)phenyl)methyloxy)-2-(N-((carbomethoxy)methyl)amino)-3,3-diphenylpropane (prepared as intermediate in Example 30, 0.5 g) and dimethylamine (2 ml) in methanol (10 ml) was stored in a sealed container at 5° C. for 72 hours and at 20° C. for 16 hours. The solvent was removed in vacuo and the residue chromatographed on silica gel (20% to 100% ethyl acetate in petroleum ether). To a methanol solution of the purified product was added a solution of hydrogen chloride in methanol and the resulting mixture evaporated to dryness and washed with diethyl ether to give the title compound as a foam. Found: C, 56.82; H, 5.13; N, 4.65; $C_{28}H_{28}N_2O_2F_6.HCl.H_2O$ requires C, 56.71; H, 5.27; N, 4.72%.

EXAMPLE 49

N-(1-((3',5'-Bis(trifluoromethyl)phenyl)methyloxy)-3,3-diphenylprop-2-yl)-N-methylglycine dimethylamide oxalate salt To a solution of 1-((3',5'-bis(trifluoromethyl)phenyl)methyloxy)-2-((carboxamido)methyl)amino -3,3-diphenylpropane (Example 30, 0.3 g) in dimethylformamide (5 ml)

was added sodium hydride (80% suspension in oil, 0.035 g) and then after 5 minutes methyl iodide (0.071 ml). After the solution had been stirred at 20° C. for 16 h, ethyl acetate (30 ml) was added and the solution washed three times with water (30 ml), saturated brine (30 ml), and dried ($MgSO_4$). The solvent was evaporated in vacuo and the residue chromatographed on silica gel (20% to 80% ethyl acetate in petroleum ether). To a solution of the purified product in methanol was added oxalic acid (40 mg), evaporated in vacuo and the residue recrystallised from ethyl acetate/ diethyl ether to give the title compound; m/e (CI+)=553 (M+H). Found: C, 56.31; H, 4.96; N, 4.18; $C_{29}H_{30}N_2O_2F_6 \cdot C_2H_2O_4 \cdot H_2O$ requires C, 56.36; H, 5.18; N, 4.28%.

EXAMPLE 50

N-(1-((3',5'-Bis(trifluoromethyl)phenyl)methyloxy)-3,3-diphenylprop-2-yl)glycine 2-hydroxyethylamide The title compound was prepared using a coupling procedure analogous to that described in Example 46 between the amino acid (Example 44, 0.24 g) and 2-aminoethanol (0.028 ml), mp 109°–111° C., m/e ($CI^+$) 555 (M+H), ($CI^-$)= 553 (M−H). Found: C, 60.45; H, 5.13; N, 5.07. $C_{28}H_{28}N_2O_3F_6$ requires C, 60.64; H, 5.09; N, 5.05%.

EXAMPLE 51

N-(1-((3',5'-Bis(trifluoromethyl)phenyl)methyloxy)-3,3-diphenylprop-2-yl)glycine 2-methoxyethylamide The title compound was prepared using a coupling procedure analogous to that described in Example 46 between the amino acid (Example 44) and 2-methoxyethylamine, m/e ($CI^+$) 569 (M+H), ($CI^-$)=567 (M−H). $^1H$ NMR (360 MHz, DMSO $d_6$) δ8.00 (1H, s), 7.97 (2H, s), 7.50 (1H, bvm), 7.45 (2H, d), 7.34–7.10 (10H, m), 4.6 (1H, d), 4.48 (1H, d), 4.09 (1H, d), 3.85 (1H, bm), 3.49 (1H, dd), 3.32 (1H, dd), 3.2 (4H, t), 3.17 (3H, s), 3.11 (1H, m).

Using analogous coupling procedures to that described in Example 46 and the amino acid (Example 44), the following were prepared:

EXAMPLE 52

N-(1-((3',5'-Bis(trifluoromethyl)phenyl)methyloxy)-3,3-diphenylprop-2-yl)glycine N',N'-dimethylethylamide bis oxalate salt m/e ($CI^+$)=582 (M+H), ($CI^-$)=580 (M−H). Found: C, 54.04; H, 5.17; N, 5.79. $C_{30}H_{33}N_3O_2F_6 \cdot 2.0(C_2H_2O_4)$ requires C, 53.62; H, 4.90; N, 5.52%.

EXAMPLE 53

N-(1-((3',5'-Bis(trifluoromethyl)phenyl)methyloxy)-3,3-diphenylprop-2-yl)glycine N'-methylpiperazinide oxalate salt m/e ($CI^+$) 594 (M+H), ($CI^-$) 593 (M). Found: C, 54.83; H, 5.49; N, 5.32. $C_{31}H_{33}N_3O_2F_6 \cdot 1.5(C_2H_2O_4) \cdot H_2O$ requires C, 54.69; H, 5.12; N, 5.62%.

EXAMPLE 54

1-((3,5-Bis(trifluoromethyl)phenyl)methyloxy)-2-((N-((methylcarboxamido)methyl)-N-methyl)amino)-3,3-diphenylpropane monohydrate The title compound was prepared in an analogous manner to that described in Example 36 from 1-((3,5-bis(trifluoromethyl)phenyl)methyloxy-2-(N-(carbomethoxy)methyl)amino-3,3-diphenylpropane (Example 30) using methylamine instead of ammonia, m/e ($CI^+$)=539 (M+H), ($CI^-$)= 537 (M−H). Found: C, 60.48; H, 5.30; N, 5.06: $C_{28}H_{28}N_2O_2F_6 \cdot H_2O$ requires C, 60.43; H, 5.43; N, 5.03%.

EXAMPLE 55

(S)-2-Dimethylammonium-1-((3,5-dimethylphenyl)methyloxy)-3,3-diphenylpropane Oxalate salt a) 2-t-Butoxycarbonyl-β,β-diphenylalanine dicyclohexylamine salt (Example 3a, 75.4 g) was liberated from its dicyclohexylamine salt by extraction in ethyl acetate from an aqueous citric acid solution, followed by washing (water and saturated brine) and drying ($MgSO_4$). The solvent was removed in vacuo to give a crystalline mass of the free acid. This solid was dissolved in dimethylformamide (200 ml) and to this solution, cooled to 0° C., was added 1-hydroxybenzotriazole (26.4 g) and 1-(3-dimethylaminopropyl)-3-ethylcarbodiimide hydrochloride (33.1 g). After stirring the solution at 0° C. for 30 minutes a solution of L-leucine methyl ester hydrochloride (31.4 g) and triethylamine (24.0 ml) in dimethylformamide (50 ml). The solution was stirred at room temperature for 16 h and then ethyl acetate (500 ml) and 10% aqueous citric acid (500 ml) were added. The organic phase was washed successively with 10% citric acid, 10% aqueous sodium carbonate, water, saturated brine and dried ($MgSO_4$). The solvent was removed in vacuo to give N-t-butyloxycarbonyl-diphenylalanyl-L-leucine methyl ester as a mixture of diastereomers (approximately 1:1). To the above solid was added anhydrous trifluoroacetic add (100 ml). After a total of 30 minutes the solvent was removed in vacuo and a solution of the residue in ethyl acetate was washed successively with 10% aqueous carbonate, saturated brine and dried ($MgSO_4$). The solvent was removed in vacuo and upon addition of ethyl acetate/hexane (1:1) gave a crystalline solid, 19.63 g formed. After removal by filtration, and recrystallisation from ethyl acetate/hexane (1:1) this gave a pure sample of D-β,β-diphenylalanyl-L-leucine methyl ester, 12.14 g.

The combined mothor liquors were evaporated to dryness and applied to a column containing silica gel. Elution with ethyl acetate/hexane (1:1) gave pure L-β,β-diphenylalanyl-L-leucine methyl ester 22.68 g as an oil.

b) L-β,β-Diphenylalanyl-L-leucine methyl ester (Example 55a, 22.5 g) was heated in a solution of 5.5M-hydrochloric acid (200 ml) at 140° C. for 24 h under an atmosphere of nitrogen. The suspension was cooled to room temperature and the solid removed by filtration and dried to give L-β,β-diphenylalanine hydrochloride, 12.42 g with an enantiomeric purity>99.0% (as determined by hplc after derivatization by (+)-9-fluorenylethylchloroformate).

c) Conversion of L-β,β-diphenylalanine hydrochloride to the title compound was by a procedure analogous to that described (Examples 1c, 1d, 1e, 1f and 2). mp=128°–129° C. from ipropanol ether, m/e ($CI^+$)=374 (M+H), ($CI^-$)=372 (M−H), $[a]_D$+36.2° (c=1 MeOH). Found: C, 72.27; H, 7.23; N, 3.18: $C_{26}H_{31}NO \cdot C_2H_2O_4$ requires C, 72.55; H, 7.18; N, 3.02%.

EXAMPLE 56

(R)-2-Dimethylammonium-1-((3,5-dimethylphenyl)methyloxy)-3,3-diphenylpropane tosylate salt D-β,β-Diphenylalanyl-L-leucine methyl ester (Example 55a) was hydrolysed and converted to the title compound as described in Example 55. mp 128°–129° C., $[a]_D$=−37.1° (c=1, MeOH). Found: C, 72.54; H, 7.07; N, 3.03. $C_{26}H_{31}NO \cdot C_2H_2O_4$ requires: C, 72.55; H, 7.18; N, 3.02%.

EXAMPLE 57

(S)-1-((3',5'-Bis(trifluoromethyl)phenyl)methyloxy)-2-(((carboxamido)methyl)ammonium)-3,3-diphenylpropane oxalate salt The title compound was prepared from L-β,β-diphenylalanine hydrochloride (Example 55b) using the procedure described (Example 30), mp=109°–111° C., m/e (FAB$^+$)=511(M+H), (FAB$^-$)=509 (M–H). Found: C, 56.41; H, 4.41; N, 4.81:$C_{26}H_{24}N_2O_2F_6$·0.95 ($C_2H_2O_4$) requires C, 56.22; H, 4.36; N, 4.67%. Enantiomeric purity>99.0% (Hplc, ULTRON® ES-OVM 35% ethanol in 10 mM ($K_2HPO_4$)).

EXAMPLE 58

1-((3',5'-Bis(trifluoromethyl)phenyl)methyloxy)-2(2S)-(1-((carboxamido)ethylamino)-3,3-diphenylpropane The title compound was prepared from L-β,β-diphenylalanine hydrochloride (Example 55b), as described in Examples 16 and 41 to give the separated diastereomers.

Diastereomer A, mp 84°–87° C.; m/e (CI$^+$)=525 (M+H), (CI$^-$)=523 (M+H). Found: C, 61.74; H, 4.99; N, 5.47.$C_{27}H_{26}F_6N_2O_2$ requires C, 61.83; H, 5.00; N, 5.34%.

Diastereomer B tosylate salt, mp 98°–100° C., m/e (CI$^+$)=525 (M+H), (CI$^-$)=523 (M–H). Found: C, 57.80; H, 5.15; N, 3.83.

$C_{27}H_{26}F_6N_2O_2$. $C_7H_8SO_3$.0.5($H_2O$). 0.5 ($CH_3COOC_2H_5$) requires C, 57.67; H, 5.24; N, 3.74%.

EXAMPLE 59

1-((3,5-Bis(trifluoromethyl)phenyl)methyloxy)-2-(((N-methylcarboxamido)methyl)amino)-3,3-diphenylpropane The title compound was prepared from 1-((3,5-bis(trifluoromethyl)phenyl)methyloxy)-2-(N-(carbomethoxymethyl)amino)-3,3-diphenylpropane (0.7 g, prepared as intermediate in Example 30) in methanol (20 ml) containing methylamine for 48 h, followed by purification by silica gel chromatography, mp=97°–100° C. Found: C, 61.54; H, 5.02; N, 5.44: $C_{27}H_{26}N_2O_2F_6$ requires C, 61.83; H, 5.00; N, 5.34%.

EXAMPLE 60

1-((3,5-Bis(trifluoromethyl)phenyl)methyloxy)-2-((N-(chloroacetamido))-3,3-diphenylpropane 2-Amino-1-((3,5-bis(trifluoromethyl)phenyl)methyloxy)-3,3-diphenylpropane (0.735 g, Example 16, liberated from the oxalate salt by partitioning between ethyl acetate and sodium carbonate solution) in toluene (20 ml) was treated with chloroacetyl chloride for 30 minutes. The product was purified by silica gel chromatography to give the title compound, mp 105°–106° C., m/e (CI$^+$)=530 (M+H). Found: C, 58.81; H, 4.08; N, 2.60. $C_{26}H_{22}NO_2ClF_6$ requires C, 58.93; H, 4.18; N, 2.64%.

EXAMPLE 61

2-(2-Ammoniumacetamido)-1-((3,5-bis(trifluoromethyl)phenyl)methyloxy)-3,3-diphenylpropane oxalate salt hemihydrate To a solution of N-benzyloxycarbonylglycine (0.23 g) and triethylamine (0.308 ml) in dichloromethane (10 ml) was added 1-hydroxybenzotriazole (0.149 g) and 1-(3-dimethylaminopropyl)-3-ethylcarbodiimide hydrochloride (0.212 g). After 5 minutes to the solution was added a solution of 2-amino-1-((3,5-bis(trifluoromethyl)phenyl)methyloxy)-3,3-diphenylpropane (Example 16, free base, 0.5 g) in dichloromethane (5 ml) and the mixture stirred at room temperature for 16 h. The organic phase was washed successively with water and saturated brine and dried (MgSO$_4$). After evaporation to dryness the residue was chromatographed on silica gel to give 2-(3-(benzyloxycarbonylamino)acetamido)-1-((3,5-bis(trifluoromethyl)phenyl)methyloxy)-3,3-diphenylpropane.

b) A solution of the compound (Example 61a, 0.55 g) in ethanol (30 ml) containing concentrated hydrochloric acid (approx 0.1 ml) was hydrogenated over 10% palladium on charcoal at 50 psi for 2 hours. The solution was filtered and after removal of the solvent from the filtrate by evaporation, the residue was dissolved in dichloromethane and washed with 2N-sodium hydroxide solution then dried (MgSO$_4$). After removal of the solvent in vacuo the residue was crystallized by addition of oxalic acid to give 2-(3-Ammoniumacetamido)-1-((3,5-bis(trifluoromethyl)phenyl)methyloxy)-3,3-diphenylpropane oxalate salt hemihydrate, m/e (CI$^+$)=511 (M+H), (CI$^-$)=509 (M–H). Found: C, 55.00; H, 4.67; N, 4.59. $C_{26}H_{24}N_2O_2F_6$. $C_2H_2O_4$.0.5$H_2O$ requires C, 55.17; H, 4.46; N, 4.59%.

EXAMPLE 62

2-(2-(Dimethylamino)acetamido)-1-((3,5-bis(trifluoromethyl)phenyl)methyloxy)-3,3-diphenylpropane A solution of 2-(2-bromoacetamido)-1-((3,5-bis(trifluoromethyl)phenyl)methyloxy)-3,3-diphenylpropane (0.36 g, prepared by an analogous procedure to that described in Example 60, from bromoacetyl chloride) in tetrahydrofuran (20 ml) and dimethylamine (1 ml) was stirred at 0° C. for 1 hour, The solution was poured onto ethyl acetate and the solution washed with water, saturated brine and dried (MgSO$_4$). After removal of the solvent in vacuo the residue was chromatographed on silica gel, followed by oxalate salt formation to give the title compound, m/e (CI$^+$)=539 (M+H), (CI$^-$)=537 (M–H).

EXAMPLE 63

1-((3,5-Bis(trifluoromethyl)phenyl)methyloxy)-3,3-diphenyl-2-(pyroglutamylamido)propane Pyroglutamic acid was coupled to the amine (Example 16) by a procedure analogous to that described (Example 61) to give the title compound, mp 135°–140° C.

EXAMPLE 64

2-(Bis((carboxamido)methyl)ammonium)-1-((3,5-bis(trifluoromethyl)phenyl)methyloxy)-3,3-diphenylpropane oxalate salt The amine (Example 16, free base, 1.6 g), K$_2$CO$_3$ (anhydrous, 1.07 g) and methyl bromoacetate (0.7 ml) in dimethylformamide (10 ml) were heated to 100° C. for 2 hours, The solution was diluted with ethyl acetate (100 ml) and this solution was washed with water (×5), saturated brine, dried (MgSO$_4$) and evaporated in vacuo. The residue was purified by silica gel chromatography to give 2-(bis((carbomethoxy)methyl)amino)-1-((3,5-bis(trifluoromethyl)phenyl)methyloxy)-3,3-diphenylpropane, as an oil. A solution of this product (0.5 g) in methanol saturated with ammonia at 0° C. (50 ml) was stored at +5° C. for 72 h. The solvent was removed in vacuo and oxalic acid (0.09 g) in ethanol added. Afar evaporation to dryness and recrystallization from diethyl ether gave the title compound, mp 159°–160° C., m/e (CI$^+$)=568 (M+H), (CI$^-$)=566 (M–H). Found: C, 56.18; H, 4.66; N, 7.13. $C_{28}H_{27}F_6N_3O_3$. 0.6($C_2H_2O_4$) requires C, 56.43; H, 4.57; N, 6.76%.

EXAMPLE 65

1-((3,5-Bis(trifluoromethyl)phenyl)methyloxy)-2-(2-(carbomethoxy)ethylamino)-3,3-diphenylpropane Methyl acrylate (10 ml) was added to the amine (Example 16, free base, 2 g) and the solution heated to reflux for 16 hours. The solution was evaporated to dryness and purified by silica gel chromatography to give the title compound as an oil. m/e (CI$^+$) 540 (M+H). Found: C, 61.84; H, 5.20; N, 2.63. $C_{28}H_{27}NO_3F_6 \cdot 0.25(H_2O)$ requires: C, 61.82; H, 5.20; N, 2.57%.

EXAMPLE 66

4-((1-((3,5-Bis(trifluoromethyl)phenyl)methyloxy)-3,3-diphenyl)prop-2-yl)piperazinium-2-one hemi oxalate salt a) A solution of 2-((2-Amino)ethylamino)-1-((3,5-bis(trifluoromethyl)phenyl)methyloxy)-3,3-diphenylpropane (Example 35, free base, 0.731 g) in $CH_2Cl_2$ (20 ml) and di-t-butyldicarbonate (0.337 g) was stirred at room temperature 1 hour and evaporated in vacuo to give 2-((2-t-butoxycarbonylamino)ethylamino)-1-((3,5-bis(trifluoromethyl)phenyl)methyloxy)-3,3-diphenylpropane b) A solution of the product (Example 66a, 0.93 g), potassium carbonate (anhydrous, 0.246 g) and methyl bromoacetate (0.174 ml) in dimethylformamide (20 ml) was heated to reflux for 2 hours. The solution was cooled to room temperature, diluted with ethyl acetate (100 ml) and solution washed with water (5×30 ml) and dried ($MgSO_4$). The solvent was removed in vacuo and the residue chromatographed on silica gel to give 1-((3,5-bis(trifluoromethyl)phenyl)methyloxy)-2-(N-((2-t-butoxycarbonylamino)ethyl)-N-((carbomethoxy)methyl)amino)-3,3-diphenylpropane.

c) The product (Example 66b, 0.48 g) was dissolved in anhydrous trifluoroacetic acid (5 ml) for 1 hour followed by removal of the solvent in vacuo. A solution of the residue dissolved in dichloromethane was washed with 2M-sodium hydroxide solution, dried ($MgSO_4$) and evaporated in vacuo. To the residue (0.3 g) dissolved in dimethylformamide (10 ml) was added sodium hydride (80% suspension in oil, 0.016 g) and the solution stirred at room temperature 1 hour and at 80° C. for 1 hour. The solution was poured onto ethyl acetate and water and the organic phase washed with water (5 times), saturated brine and dried ($MgSO_4$). After removal of the solvent in vacuo the residue was purified by chromatography on silica gel followed by oxalate salt formation to give 4-((1-((3,5-bis(trifluoromethyl)phenyl)methyloxy)-3,3-diphenyl)prop-2-yl)piperazinium-2-one hemi oxalate salt, m/e (FAB$^+$)=537 (M+H). Found: C, 60.03; H, 4.73; N, 5.08. $C_{28}H_{26}N_2O_2F_6 \cdot 0.5(C_2H_2O_4)$ requires C, 59.90; H, 4.68; N, 4.82%.

EXAMPLE 67

2-Amino-3,3-diphenyl-N-((3,5-bis(trifluoromethyl)phenyl)methyl)propionamide a) To a solution of 3,5-bis(trifluoromethyl)benzylamine (5 g) in tetrahydrofuran (100 ml) was added N-t-butoxycarbonyl-β,β-diphenylalanine (Example 3a, 8.42 g, liberated from the dicyclohexylamine salt by extraction into ethyl acetate from aqueous citric acid solution), 1-hydroxybenzotriazole hydrate (3.33 g) and 1-(3-dimethylaminopropyl)-3-ethylcarbodiimide hydrochloride (4.74 g). After the solution had been stirred at room temperature for 18 hours the solvent was removed in vacuo and a solution of the residue in ethyl acetate washed successively with aqueous citric acid (three times), 5% sodium bicarbonate solution, saturated brine and dried ($MgSO_4$). Upon removal of the solvent in vacuo this gave 2-t-Butoxycarbonylamino-2,2-diphenyl-N-((3,5-bis-(trifluoromethyl)phenyl)methyl)propionamide. $^1$H NMR (360 MHz, CDCl$_3$) δ1.35 (9H, s, CH$_3$), 4.34 (2H, d, J=5.93 Hz, NCH$_2$), 4.53 (1H, d, J=8.10 Hz, CHPhPh), 4.84 (1H, dd, CHCO), 4.95 (1H, br s, NHCOO$^+$Bu), 6.19 (1H, t, CON HCH$_2$), 7.14–7.29 (10H, m, ArH), 7.52 (2H, s, ArH), 7.75 (1H, s, ArH); MS (CI$^+$) m/z 566 ((M=1)$^+$ 10%).

b) The product (Example 67a, 11,64 g) was dissolved in trifluoroacetic acid (50 ml) for 20 minutes followed by evaporation in vacuo to give an orange oil. The residue was dissolved in ethyl acetate and the solution washed with dilute ammonia solution, dried ($MgSO_4$) and evaporated to dryness. The residue was purified by chromatography on silica gel (eluting with 1% aqueous ammonia, 2% methanol in dichloromethane) followed by recrystallization from diethyl ether/petroleum ether bp 60°–80° C. to give the title compound. $^1$H NMR (250 MHz, CDCl$_3$) δ2.37 (2H, s, NH$_2$), 4.19 (1H, d, J=7.9 Hz, CHPhPh), 4.33 (1H, dd, J=9.0 Hz, 22.3 Hz, NHCHH), 4.47 (1H, dd, J=9.0 Hz, 22.3 Hz, NHCH H), 4.66 (1H, d, J=7.9 Hz, CHNH$_2$), 7.10–7.29 (10H, m, ArH), 7.58 (2H, s, ArH), 7.77 (1H, s, ArH); MS (CI$^+$) m/z 466 ((M+1)$^+$ 100%).

EXAMPLE 68

2-Ammonium-3,3-diphenyl-1-((3-methyl, 5-trifluoromethyl)phenyl)methylamino)propane oxalate salt To a solution of the product (Example 67b, 1 g) in tetrahydrofuran (30 ml) was slowly added to a stirred solution of lithium aluminium hydride (1M in tetrahydrofuran; 6.4 ml) at 0° C. under nitrogen. The mixture was refluxed for 18 h. The reaction mixture was cooled to 0° C. and excess lithium aluminium hydride was destroyed by consecutive addition of water (0.7 ml), 15% aqueous sodium hydroxide solution (0.7 ml) and water (2 ml). The precipitate which formed was removed by filtration and the filtrate was concentrated in vacuo to give an oil. Di-t-butyldicarbonate (0.49 g) was added to 0.34 g of the product dissolved in dichloromethane (10 ml) and the mixture was stirred for 65 h. The solvent was removed in vacuo and the residue was purified by chromatography on silica using 5% ethyl acetate in hexane as eluant. This afforded an oil to which trifluoroacetic acid (5 ml) was added. After stirring for 10 min excess trifluoroacetic acid was removed in vacuo. The material was dissolved in water/methanol and 15% aqueous sodium hydroxide solution was added until the reaction mixture was basic. Methanol was removed in vacuo and the product was extracted into ethyl acetate. The organic layer was dried ($Na_2SO_4$) and concentrated to give the free base. This was dissolved in minimum amount of methanol and a solution of anhydrous oxalic acid (0.13 g) in ether (10 ml) was added. The resulting precipitate was filtered to give the title compound. $^1$H NMR (360 MHz, DMSO) δ2.53 (3H, s, CH$_3$), 2.63 (2H, brs, CH$_2$Ar), 3.75 (1H, d, J=13.8 Hz, C HPhPh), 3.89 (1H, d, J=13.8 Hz, CHNH$_2$), 4.10 (1H, d, J=11.4 Hz, CHCHHNH), 4.25–4.35 (1H, m, CHCHHNH), 7.11–7.55 (13H, m, ArH); MS (FAB m/z 398 (CM+1)$^+$ 58%). :

EXAMPLE 69

1-((3,5-Bis(trifluoromethyl)phenyl)methyloxy)-3,3-diphenyl-2-methylsulphonamidopropane To a solution of the amine (Example 16, free base, 0.5 g) in dichloromethane (30 ml) was added methanesulphonyl chloride (0.128 ml) and triethylamine (0.23 ml) for 16 hours. The solvent was removed in vacuo and the residue purified by chromatography on silica gel (eluting with ethyl acetate/ petroleum ether, bp=60°–80° C.) to give a mixture of 1((3,5-bis(trifluoromethyl)methyloxy)-3,3-diphenyl-2-methylsulphonamidopropane and 1-((3,5-bis(trifluoromethyl)methyloxy)-3,3 -diphenyl-2-(N,N-bis(methanesulphonyl)amino)propane, m/e (CI⁺) 549 (M+NH⁺₄).

EXAMPLE 70

2-Amino-1-((3,5-bis(trifluoromethyl)phenyl)methyloxy)-3-(3-methoxyphenyl)-4-phenylbutane a) To a solution of (3-methoxyphenyl)acetylchloride (25 g, 135 mmol), in dry dichloromethane (50 ml) was added t-butanol (14 ml) slowly with stirring. After stirring at room temperature for 5 minutes, the reaction was cooled in ice, and triethylamine (20 ml) added dropwise. After stirring a further 2 hours at room temperature, the reaction was poured into saturated aqueous sodium carbonate solution, extracted with dichloromethane, dried (MgSO₄), solvents evaporated, and the residue chromatographed on silica (eluted 10% diethyl ether-petroleum ether bp 60°–80°), to give t-butyl (3-methoxyphenyl)acetate. ¹H NMR (250 MHz, CDCl₃) δ1.38 (9H, s), 3.42 (2H, s), 3.73 (3H, s), 6.69–6.82 (3H, m), 7.17 (1H, t, J=8.4Hz).

b) To a solution of potassium bis(trimethylsilyl)amide (70 ml of a 0.6M solution in toluene) at –70° C. under nitrogen was added dripwise over 30 minutes a solution of the product of Example 70a (8.9 g, 40 mmol) in dry tetrahydrofuran (40 ml). After stirring a further 1 hour at –78° C. benzyl bromide (5.25 ml) was added, and the reaction allowed to warm slowly to room temperature over 2 hours. The reaction was then poured into water, and extracted with diethyl ether. The extracts were dried (MgSO₄), concentrated, and the residue subjected to chromatography on silica (eluent 10% diethyl ether-petroleum ether b.p. 60–80) to afford t-buryl 2(3-methoxyphenyl)-3-phenyl-propionate. ¹H NMR (250 MHz, CDCl₃) δ1.30 (9H, s), 2.96 (1H, dd, J=5.6, 14.0 Hz), 3.32 (1H, dd, J=9.6, 14.0 Hz), 3.74 (1H, dd, J=5.6, 9.6 Hz), 3.79 (3H, s), 6.8 (1H, m), 6.86–6.94 (2H, m), 7.12–7.29 (6H, m).

c) The product of Example 70b (0.16 g) was dissolved in trifluoroacetic acid (10 ml), and allowed to stand at room temperature for 1 hour. After evaporation at reduced pressure, toluene (20 ml) was added, and then removed by evaporation at reduced pressure, to give 2-(3-methoxyphenyl)-3-phenylpropionic acid. ¹H NMR (360 MHz, CDCl₃) δ3.02 (1H, dd, J=6.8, 13.7 Hz), 3.38 (1H, dd, J=8.5, 13.7 Hz), 3.77 (3H, s), 3.81 (1H, dd, J=6.7, 8.5 Hz), 6.79–6.90 (3H, m), 7.10–7.27 (6H, m).

d) The product of Example 70c (7.79 g) was dissolved in thionyl chloride (15 ml). N,N-Dimethylformamide (50 µl) was added, and the mixture allowed to stand at room temperature for 4 hours. Residual thionyl chloride was then evaporated at reduced pressure, the residue dissolved in toluene (40 ml) and again evaporated at reduced pressure, to give 2-(3-methoxyphenyl)-3-phenylpropionyl chloride.

e) To a distilled solution of diazomethane (32 mmol) in dry diethyl ether (120 ml) at 0° C. was added dropwise over 10 minutes a solution of the product of Example 70d (3.2 g) in diethyl ether (30 ml). The reaction was then allowed to stand at room temperature for 2 hours. Excess diazomethane was removed by passing a stream of nitrogen through the solution for 30 minutes. The mixture was then evaporated at reduced pressure to give 3-(3-methoxyphenyl)-4-phenyl-1-diazo-2-butanone.

f) To a solution of 3,5-bis(trifluoromethyl)benzyl alcohol (6 g) in benzene (8 ml) and Rh₂(CH₃CO₂)₄ (20 mg) at reflux under an argon atmosphere, was added dropwise over 4 hours a solution of the product of Example 70e. The mixture was heated at reflux for a further 1 hour, cooled, and evaporated at reduced pressure. The residue was chromatographed on silica (eluent 5% diethyl ether-petroleum ether 60–80 b.p.) to give 1-((3,5-bis(trifluoromethyl)phenyl)methyloxy)-3-(3-methoxyphenyl)-4-phenyl-2-butanone. ¹H NMR (360 MHz, CDCl₃) δ2.94 (1H, dd, J=6.19, 13.6 Hz), 3.45 (1H, dd, J=9.0, 13.6 Hz), 3.77 (3H, s), 3.97 (1H, d, J=17 Hz), 4.06 (1H, m), 4.08 (1H, d, J=17 Hz), 4.38 (2H, ABQ), 6.75–6.83 (3H, m), 7.08–7.26 (6H, m), 7.66 (2H, s), 7.78 (1H, s).

g) To the product of Example 70f in methanol (3 ml) was added hydroxylamine hydrochloride (325 mg) and triethylamine (770 µl). The mixture was allowed to stir at room temperature for 3 days. The methanol was evaporated at reduced pressure, and the residue partitioned between water and ethyl acetate. The organic extracts were dried (MgSO₄), evaporated, and the residue chromatographed on silica (eluent 20% diethyl etherpetroleum ether 60–80 b.p.), to give 1-((3,5-bis(trifluoromethyl)phenyl)methyloxy)-3-(3-methoxyphenyl)-4-phenyl-2-butanone oxime.

h) The product of Example 70 g (152 mg) was dissolved in borane tetrahydrofuran complex (10 ml of a 1.0M solution in tetrahydrofuran), and the mixture heated at reflux for 36 hours. On cooling, the reaction was evaporated at reduced pressure, the residue treated with methanol (10 ml) added dropwise, followed by dropwise addition of 2.0M hydrochloric acid (1 ml). The mixture was allowed to stand 1 hour, and the solvents evaporated at reduced pressure. The residue was dissolved in ethanol (20 ml) and hydrogenated over 10% palladium-carbon catalyst under an atmosphere of hydrogen at 50 p.s.i. for 5 hours. After filtration and evaporation at reduced pressure, the residue was treated with dichloromethane and saturated aqueous sodium carbonate solution. After drying (Na₂SO₄), the organic phase was evaporated and the residue chromategraphed on neutral alumina (eluent gradient from 40% diethyl etherpetroleum ether 60–80 b.p. to neat diethyl ether) to give as a 1:1 mixture of diastereoisomers 2-amino-1-((3,5-bis(trifluoromethyl)phenyl)methyloxy)-3-(3-methoxyphenyl)-4-phenylbutane.

Diastereoisomer A: ¹H NMR (360 MHz, CDCl₃) δ2.86 (1H, m), 2.88 (1H, m), 3.18 (1H, dd), 3.28 (1H, dd), 3.33 (1H, dd), 3.39 (1H, dd), 3.71 (3H, s), 4.44 (1H, d), 4.49 (1H, d), 6.59 (1H, m), 6.64 (1H, d), 6.69 (1H, dd), 6.97 (2H, d), 7.12 (1H, dd), 7.12–7.22 (3H, m), 7.72 (2H, s), 7.79 (1H, s). m/e (CI⁺) 512 (M+H).

Diastereoisomer B: ¹H NMR (360 MHz, CDCl₃) δ2.94 (1H, dd), 3.04 (1H, dd), 3.15 (1H, dd), 3.23 (1H, dd), 3.36 (1H, dd), 3.53 (1H, dd), 3.75 (3H, s), 4.51 (1H, d), 4.56 (1H, d), 6.74 (1H, m), 6.75 (1H, dd), 6.78 (1H, d), 7.07 (2H, d), 7.12–7.22 (3H, m), 7.18 (1H, dd), 7.76 (2H, s), 7.90 (1H, s). m/e (CI⁺) 512 (M+H).

EXAMPLE 71

2-Amino-1-((3,5-bis(trifluoromethyl)phenyl)methyloxy)-3-(3-chlorophenyl)-butane a) To 3-chlorophenylacetic acid (51 g) was added thionyl chloride (100 ml) and N,N-dimethylforraamide (50 µl). After stirring at room temperature for 18 hours, the thionyl chloride was evaporated at reduced pressure. The residue was dissolved in toluene (60 ml) and again evaporated at reduced pressure to give 3-chlorophenylacetylchloride.

b) The product of Example 71a was converted to 1-((3,5-bis(trifluoromethyl)phenyl)methyloxy)-3-(3-chlorophenyl)-2-butanone in a manner analagous to that described in Example 70a, b, c, d, e and f.

c) To a solution of the product of Example 71b (630 mg) in methanol (5 ml), and triethylamine (240 µl), was added O-benzylhydroxylamine hydrochloride (260 mg), and the mixture stirred at room temperature for 72 hours. The solvent was evaporated at reduced pressure, and the residue dissolved in ether, washed with water. The organic phase was dried ($Na_2SO_4$), evaporated, and the residue chromatographed on silica (eluent 10% diethyl ether-petroleum ether 60–80 b.p.) to give 1-((3,5-bis(trifluoromethyl)phenyl)methyloxy)-3-(3-chlorophenyl)-2-butanone O-benzyloxime. m/e ($CI^+$) 532 (M+H), 530 (M+H).

d) The product of Example 71c (360 mg) was dissolved in borane tetrahydrofuran complex (10 ml of a 1.0M solution in tetrahydrofuran), and the mixture heated at reflux for 18 hours. On cooling, methanol was added dropwise until hydrogen evolution ceased. The mixture was then evaporated at reduced pressure, and the residue treated with methanolic hydrogen chloride. The solvent was evaporated at reduced pressure, and the residue partitioned between ethyl acetate and saturated aqueous sodium carbonate solution. The organic layer was dried ($Na_2SO_4$), evaporated, and the residue chromatographed on silica (eluent ethyl acetate) to give the two diastereoisomers of 2-amino-1-((3,5-bis(trifluoromethyl)phenyl)methyloxy)-3-(3-chlorophenyl)-butane.

Diastereoisomer A: $^1$H NMR (360 MHz, $CDCl_3$) δ1.27 (3H, d, J=7 Hz), 2.80 (1H, m), 3.15 (1H, m), 3.45 (1H, dd, J=6.8, 9.0 Hz), 3.61 (1H, dd, J=3.8, 9.0 Hz), 4.64 (2H, ABQ), 7.10–7.27 (4H, m), 7.79 (2H, s), 7.81 (1H, s). m/e ($CI^+$) 428 (M+H), 426 (M+H) (1:3).

Diastereoisomer B: $^1$H NMR (360 MHz, $CDCl_3$) δ1.32 (3H, d, J=7 Hz), 2.75 (1H, m), 3.12 (1H, m), 3.22 (1H, dd, J=7.0, 9.0 Hz), 3.37 (1H, dd, J=3.5, 9.0 Hz), 4.51 (2H, ABQ), 7.05–7.26 (4H, m), 7.74 (2H, s), 7.79 (1H, s). m/e ($CI^+$) 428 (M+H), 426 (M+H) (1:3).

EXAMPLE 72

1-((3,5-Bis(trifluoromethyl)phenyl)methyloxy)-2-(N-((carboxamido)methyl)-N-methyl)ammonium-3,3-diphenylpropane oxalate salt a) 1-((3,5-Bis(trifluoromethyl)phenyl)methyloxy)-2-(t-butoxycarbonylamino)-3,3-diphenylpropane (prepared as intermediate in Example 16) was N-methylated and deprotected by an analogous procedure to that described in Example 6 to give 1-((3,5-bis(trifluoromethyl)phenyl)methyloxy)-2-(N-methyl)amino-3,3-diphenylpropane.

b) The compound prepared in Example 72a was treated with methyl bromoacetate (as described in Example 20) and ammonia (as described in Example 21) to give the title compound, mp 66°–68° C., m/e ($CI^+$)=525 (M+H), ($CI^-$)= 524 (M–H). Found: C, 55.43; H, 4.69; N, 4.32: $C_{27}H_{26}F_6N_2O_2 \cdot C_2H_2O_4 \cdot 0.7H_2O$ requires C, 55.54; H, 4.72; N, 4.46%.

EXAMPLE 73

(2S)-1-((3,5-Bis(trifluoromethyl)phenyl)methyloxy)-2-((N-((methylcarboxamido)methyl)-N-methyl)amino)-3,3-diphenylpropane The title compound was prepared from (2S)-1-((3,5-bis(trifluoromethyl)phenyl)methyloxy)-2-((N-(carbomethoxy)methyl)-N-methyl)amino)-3,3-diphenylpropane (Example 74a) and methylamine by a procedure analogous to that described in Example 21, mp=89°–92° C.

EXAMPLE 74

(2S)-1-((3,5-Bis(trifluoromethyl)phenyl)methyloxy)-2-((N-((N-(2-methoxyethyl)carboxamido)methyl)-N-methyl)amino)-3,3-diphenylpropane a) To a solution of (2S)-1-((3,5-bis(trifluoromethyl)phenyl)methyloxy)-2-(N-(carbomethoxy)methylamino-3,3-diphenylpropane (7.6 g, prepared as an intermediate in Example 57) in dimethylformamide (80 ml) was added potassium carbonate (10 g) and methyl iodide (4.5 ml) and the solution stirred in an enclosed atmosphere for 16 hours. Ethyl acetate (200 ml) and water were added and the organic phase washed with water, brine and dried ($MgSO_4$). Purification by silica gel chromatography gave (2S)-1-((3,5-bis-(trifluoromethyl)phenyl)methyloxy)-2-((N-(carbomethoxy)methyl)-N-methyl)amino)-3,3-diphenylpropane.

b) A solution of the product of Example 74a (0.152 g) and 2-methoxyethylamine (0.41 ml) in dimethylformamide (3 ml) was heated at 150° C. for 22 h, cooled to room temperature and diluted by addition of ethyl acetate (100 ml) and water (50 ml). The organic phase was washed repeatedly with water, saturated brine and dried ($MgSO_4$). The product was purified by silica gel chromatography to give the title compound as an oil. $^1$H NMR (250 MHz, $CDCl_3$) 7.80 (1H, s), 7.68 (2H, s), 7.4–7.12 (10H, m), 6.36 (1H, bt), 4.44 (1H, d), 4.36 (1H, d), 4.06 (1H, d), 3.7 (1H, m), 3.58–3.38 (3H, m), 3.24 (3H, s), 3.2–3.0 (5H, m), 2.34 (3H, s).

The following examples illustrate pharmaceutical compositions according to the invention.

EXAMPLE 75A

Tablets containing 1–25 mg of compound

|  | Amount mg | | |
| --- | --- | --- | --- |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 75B

Tablets containing 26–100 mg of compound

|  | Amount mg | | |
| --- | --- | --- | --- |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 76

Parenteral injection

|  | Amount mg |
| --- | --- |
| Compound of formula (I) | 1 to 100 mg |
| Citric Acid Monohydrate | 0.75 mg |
| Sodium Phosphate | 4.5 mg |
| Sodium Chloride | 9 mg |
| Water for injection | to 1 ml |

The sodium phosphate, citric acid monohydrate and sodium chloride are dissolved in a portion of the water. The compound of formula (I) is dissolved or suspended in the solution and made up to volume.

EXAMPLE 77

Topical-formulation

|  | Amount mg |
| --- | --- |
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

SUBSTANCE P ANTAGONISM ASSAY

A. Receptor Expression in Monkey Kidney Cell Line (COS)

To express the cloned human neurokinin-1-receotor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+ (trademark, STRATAGENE, La Jolla, Calif., U.S.A.)) into the Sac II site. Transfection of 20 ug of the plasmid DNA into 10 million COS cells was achieved by electroporation in 800 μl of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM N-2-hydroxyethyl-piperazine-N'-2-ethane sulphonic acid (HEPES) pH 7.4) at 260 V and 950 μF using the IBI GENEZAPPER (trademark IBI, New Haven, Conn., U.S.A.). The cells were incubated in 10% fetal calf serum, 2 mM glutamine, 100 U/ml penicillin-streptomycin, and 90% DMEM media (GIBCO, Grand Island, N.Y., U.S.A.) in 5% $CO_2$ at 37° C. for three days before the binding assay.

B. Stable Expression in Chinese Hamster Ovarian Cell Line

To establish a stable cell line expressing cloned human NK1R, the cDNA was subcloned into the vector pRcCMV (INVITROGEN). Transfection of 20 ug of the plasmid DNA into CHO cells was achieved by electroporation in 800 μl of transfection buffer supplemented with 0.625 mg/ml Herring sperm DNA at 300 V and 950 μF using the IBI GENEZAPPER (IBI). The transfected cells were incubated in CHO media [10% fetal calf serum, 100 U/ml penicillin-streptomycin, 2 mM glutamine, 1/500 hypoxanthinethymidine (ATCC), 90% IMDM media (JRH BIOSCIENCES, Lenexa, Kans., U.S.A.), 0.7 mg/ml G418 (GIBCO)] in 5% $CO_2$ at 37° C. until colonies were visible. Each colony was separated and propagated. The cell clone with the highest number of human NK1R was selected for subsequent applications such as drug screening.

C. Assay Protocol using COS or CHO

The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavellette, N.J.) and resuspended in appropriate volume of the binding buffer (50 mMTris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 μl of the cell suspension would give rise to about 10,000 cpm of specific $^{125}$I-SP binding (approximately 50,000 to 200,000 cells). In the binding assay, 200 ul of cells were added to a tube containing 20 ul of 1.5 to 2.5 nM of $^{125}$I-SP and 20 μl of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was prewetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter.

The activation of phospholiphase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 5 μCi of $^3$H-myoinositol in 1 ml of media per well by overnight incubation. The extracellular radioactivity is removed by washing with phosphate buffered saline. LiCl is added to the well at final concentration of 10 mM with or without the test compound, and incubation is continued at 37° C. for 15 min. Substance P is added to the well at final concentration of 0.3 nM to activate the human NK1R. After 30 min of incubation at 37° C., the medium is removed and 0.1N HCl is added. Each well is sonicated at 4° C. and extracted with $CHCl_3$/methanol (1:1). The aqueous phase is applied to a 1 ml Dowex AG 1X8 ion exchange column. The column is washed with 0.1N formic acid followed by 0.025M ammonium formate-0.1N formic acid. The inositol monophosphate is eluted with 0.2M ammonium formate-0.1N formic acid and quantitated by beta counter.

The data in Table 1 were obtained for compounds of formula (I):

TABLE 1

SUBSTANCE P ANTAGONISM RESULTS

| Compound of Ex # | $IC_{50}$ @ NK1R (nM) |
| --- | --- |
| 1 | 5.5 |
| 2 | 2.4 |
| 3 | 77% @ 10 μM |
| 4 | 700 |
| 5 | 160 |
| 6 | 10 |
| 7 | 20 |
| 8 | 90 |
| 9 | 100 |
| 10 | 70 |
| 11 | 320 |
| 12 | 19 |
| 13 | 20 |
| 14 | 70 |
| 15 | 100 |
| 16 | 9 |
| 17 | 5 |
| 18 | 22 |
| 19 | 120 |
| 20 | 40 |
| 21 | 3 |
| 22 | 45 |
| 23 | 35 |
| 24 | 400 |
| 25 | 600 |
| 26 | 140 |
| 27 | 70 |
| 28 | 300 |
| 29 | 48% @ 1 μM |
| 30 | 0.4 |
| 31 | 200 |
| 32 | 30 |

TABLE 1-continued

SUBSTANCE P ANTAGONISM RESULTS

| Compound of Ex # | IC$_{50}$ @ NKIR (nM) |
| --- | --- |
| 33 | 20 |
| 34 | 10 |
| 35 | 5 |
| 36 | 7 |
| 37 | 200 |
| 38 | 70 |
| 39 | 800 |
| 40 | 580 |
| 41 (diastereomer A) | 0.4 |
| 41 (diastereomer B) | 0.5 |
| 42 | 40 |
| 43 | 50% @ 03 μM |
| 44 | 15 |
| 45 | 40 |
| 46 | 4 |
| 47 | 15 |
| 48 | 10 |
| 49 | 15 |
| 50 | 1 |
| 51 | 1 |
| 52 | 1 |
| 53 | 5 |
| 54 | 2 |
| 55 | 2 |
| 56 | 18 |
| 57 | 0.8 |
| 58 (diastereomer A) | 0.4 |
| 58 (diastereomer B) | 0.5 |
| 59 | 1.5 |
| 60 | 80 |
| 61 | 30 |
| 62 | 200 |
| 63 | 30 |
| 64 | 5 |
| 65 | 35 |
| 66 | 4 |
| 67 | 220 |
| 68 | 400 |
| 69 | 35 |
| 70 (mixture of diastereomers) | 160 |
| 71 (diastereomer B) | 42% @ 0.3 μM |
| 72 | 7 |
| 74 | 2 |
| 74 | NT |

NT = not tested

We claim:

1. A compound of formula (I), or a pharmaceutically acceptable salt or prodrug thereof:

(I)

wherein

Q represents $R^9CR^{10}R^{11}$ where $R^9$ is H or hydroxy and $R^{10}$ and $R^{11}$ each independently represent optionally substituted phenyl, optionally substituted benzyl, $C_{5-7}$cycloalkyl or ($C_{5-7}$cycloalkyl)methyl;

$R^1$ represents H or $R^2$;

$R^2$ independently represents $C_{1-6}$ alkyl substituted by CONR$^a$R$^b$, CONR$^{12}$C$_{1-6}$alkylOR$^a$ or CONR$^{12}$C$_{1-6}$alkylCONR$^a$R$^b$ (where R$^a$ and R$^b$ each independently represent H, $C_{1-6}$ alkyl, phenyl (optionally substituted by one or more of $C_{1-6}$alkyl, $C_{1-6}$alkoxy, halo and trifluoromethyl), phenyl($C_{1-4}$alkyl) (optionally substituted in the phenyl ring by one or more of $C_{1-6}$ alkyl, $C_{1-6}$ alkoxy, halo and trifluoromethyl), and $R^{12}$ represents H, $C_{1-6}$alkyl, phenyl (optionally substituted by one or more of $C_{1-6}$alkyl, $C_{1-6}$alkoxy, halo and trifluoromethyl) or phenyl($C_{1-4}$alkyl) (optionally substituted in the phenyl ring by one or more of $C_{1-6}$alkyl, $C_{1-6}$alkoxy, halo and trifluoromethyl);

$R^3$ represents H, $C_{1-6}$ alkyl or $C_{2-6}$alkenyl;

$R^4$ represents $C_{1-3}$ alkyl substituted by a phenyl group which may itself optionally be substituted by one or more of $C_{1-6}$ alkyl, $C_{2-6}$ alkenyl, $C_{2-6}$ alkynyl, halo, cyano, nitro, trifluoromethyl, SR$^c$, SOR$^c$, OR$^c$, NR$^c$R$^d$, NR$^c$COR$^d$, and CONR$^c$R$^d$, where R$^c$ and R$^d$ independently represent H, $C_{1-6}$ alkyl, phenyl or trifluoromethyl;

X and Y each represent H, or X and Y together represent a group =O; and

Z represents O, S, or NR$^7$, where R$^7$ represents H or $C_{1-6}$ alkyl;

with the exception of DL-diphenylalanine benzyl ester, or the hydrochloride salt thereof; 2-benzamido-3,3-diphenylpropanoyl benzamide; and 2-benzamido-3,4-diphenyl-butanoyl benzamide.

2. A compound as claimed in claim 1 of formula (Ia)

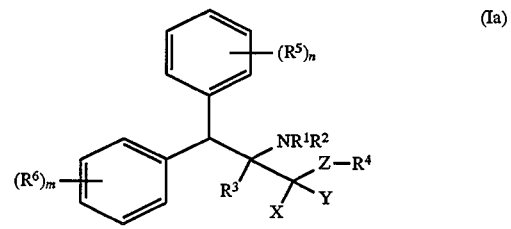

(Ia)

wherein $R^1$ represents H or $R^2$ $R^2$ independently represents $C_{1-6}$ alkyl substituted by CONR$^{13}$R$^{14}$, CONR$^{13}$C$_{1-4}$alkylOR$^{14}$, or CONR$^{13}$C$_{1-4}$alkylCONR$^{13}$R$^{14}$ (where $R^{13}$ and $R^{14}$ each independently represent H, $C_{1-6}$ alkyl, phenyl (optionally substituted by one or more of $C_{1-6}$alkyl, $C_{1-6}$alkoxy, halo and trifluoromethyl), or phenyl($C_{1-4}$alkyl) (optionally substituted in the phenyl ring by one or more of $C_{1-6}$ alkyl, $C_{1-6}$ alkoxy, halo and trifluoromethyl);

$R^3$ represents H or $C_{1-6}$ alkyl;

$R^4$ represents $C_{1-3}$ alkyl substituted by a phenyl group which may itself optionally be substituted by one or more of $C_{1-6}$ alkyl, $C_{2-6}$ alkenyl, $C_{2-6}$ alkynyl, halo, cyano, nitro, trifluoromethyl, SCH$_3$, SOCH$_3$, OR$^c$, NR$^c$R$^d$, NR$^c$COR$^d$, and CONR$^c$R$^d$, where R$^c$ and R$^d$ independently represent H, $C_{1-6}$ alkyl, phenyl or trifluoromethyl each $R^5$ independently represents $C_{1-6}$ alkyl, $C_{1-6}$ alkoxy, halo or trifluoromethyl;

each $R^6$ independently represents $C_{1-6}$ alkyl, $C_{1-6}$ alkoxy, halo or trifluoromethyl;

n and m each represent 0, 1, 2 or 3;

X and Y each represent H, or X and Y together represent a group =O; and

Z represents O, S, or NR$^7$, where R$^7$ represents H or $C_{1-6}$ alkyl; or a pharmaceutically acceptable salt or prodrug thereof.

3. A compound as claimed in claim 1 wherein at least one of $R^1$ and $R^2$ represents an alkyl chain selected from CH$_2$, CH(CH$_3$), C(CH$_3$)$_2$, CH(CH$_2$CH$_3$), C(CH$_3$)(CH$_2$CH$_3$), CH(CH$_2$CH$_2$CH$_3$) and CH(CH(CH$_3$)$_2$), substituted by a group selected from CONR$^a$R$^b$, CONR$^{12}$C$_{1-4}$alkylCONR$^a$R$^b$ and CONR$^2$C$_{1-4}$alkylOR$^a$, wherein R$^a$, R$^b$ and R$^{12}$ are as defined for formula (I).

4. A compound as claimed in claim 1 wherein X and Y each represent H and Z represents O.

5. A compound as claimed in claim 1 wherein $R^4$ represents $CH_2$ substituted by a phenyl group substituted by two substituents selected from H, $C_{1-6}$ alkyl, $C_{2-6}$ alkenyl, $C_{1-6}$ alkoxy, halo, cyano, nitro, trifluoromethyl, $SR^c$, $SOR^c$, $SOR^c$, $NR^c$, $R^d$, $NR^cCOR^d$, and $CONR^cR^d$, where $R^c$ and $R^d$ are as previously defined.

6. A compound selected from
2-(((carboxamido)methyl)amino)-1-((3,5-dimethylphenyl) methyloxy)-3,3-diphenylpropane;
1-((3,5-bis(trifluoromethyl)phenyl)methyloxy)-2-(((carboxamido)methyl)-ammonium)-3,3-diphenylpropane;
2-(N((carboxamido)methyl)-N-methyl)ammonium-1-((3,5-dimethylphenyl)methyloxy)-3,3-diphenylpropane;
1-((3,5-bis(trifluoromethyl)phenyl)methyloxy)-2-((1-(carboxamido)ethyl)-ammonium)-3,3-diphenylpropane;
N-(1-(((3,5-bis(trifluoromethyl)phenyl)methyloxy)-3,3-diphenylprop-2-yl)glycylglycine amide;
N-(1-((3,5-bis(trifluoromethyl)phenyl)methyloxy)-3,3-diphenylprop-2-yl)glycylbenzamide;
N-(1-((3,5-bis(trifluoromethyl)phenyl)methyloxy)-3,3-diphenylprop-2-yl)glycine dimethylamide;
N-(1-((3,5-bis(trifluoromethyl)phenyl)methyloxy)-3,3-diphenylprop-2-yl)-N-methylglycine dimethylamide;
N-(1-((3,5-bis(trifluoromethyl)phenyl)methyloxy)-3,3-diphenylprop-2-yl)glycine 2-hydroxyethylamide;
N-(1-((3,5-bis(trifluoromethyl)phenyl)methyloxy)-3,3-diphenylprop-2-yl)glycine 2-methoxyethylamide;
N-(1-((3,5-bis(trifluoromethyl)phenyl)methyloxy)-2-((N-((methylcarboxamido)-methyl)-N-methyl)amino)-3,3-diphenylpropane
(S)-1-((3,5-bis(trifluoromethyl)phenyl)methyloxy)-2-(((carboxamido)methyl)-ammonium)-3,3-diphenylpropane;
1-((3,5-bis(trifluoromethyl)phenyl)methyloxy)-2-(2S)-(1-((carboxamido)ethyl)-amino)-3,3-diphenylpropane;
1-((3,5-bis(trifluoromethyl)phenyl)methyloxy)-2-(((N-methylcarboxamido)-methyl)amino)-3,3-diphenylpropane;
2-(bis((carboxamido)methyl)ammonium)-1-((3,5-bis(trifluoromethyl)phenyl)-methyloxy)-3,3-diphenylpropane;
1-((3,5-bis(trifluoromethyl)phenyl)methyloxy)-2-(N-((carboxamido)methyl)-N-methyl)ammonium-3,3-diphenylpropane;
(2S)-1-((3,5-bis(trifluoromethyl)phenyl)methyloxy)-2-((N-((N-(2-methoxyethyl)-carboxamido)methyl)-N-methyl)amino)-3,3-diphenylpropane;

and pharmaceutically acceptable salts and prodrugs thereof.

7. A compound selected from(2S)-1-((3,5-bis(trifluoromethyl)phenyl)methyloxy)-2-((N-((methylcarboxamido)methyl)-N-methyl)amino)-3,3-diphenylpropane;

and pharmaceutically acceptable salts and prodrugs thereof.

8. A process for the preparation of a compound as claimed in claim 1, which process comprises:

(A) reaction of a compound of formula (II):

wherein Q, $R^1$, $R^2$, $R^3$, X and Y are defined as for formula (I) and Z is O or S, with a compound of formula $R^4Hal$ where $R^4$ is defined as for formula (I) and Hal is halo; or (B) reaction of a compound of formula (II) wherein Z is O with a compound of formula $HNR^7R^4$, where $R^7$ and $R^4$ are as defined for formula (I); or a pharmaceutically acceptable salt or prodrug thereof.

9. A method for the treatment of a physiological disorder associated with an excess of tachykinins, which method comprises administration to a patient in need thereof of a tachykinin reducing amount of a compound according to claim 1.

10. A method according to claim 9 wherein said physiological disorder is pain or inflammation.

11. A method according to claim 9 wherein said physiological disorder is migraine.

12. A method according to claim 9 wherein said physiological disorder is postherpetic neuralgia.

* * * * *